US009339220B2

(12) United States Patent
Lamego et al.

(10) Patent No.: US 9,339,220 B2
(45) Date of Patent: *May 17, 2016

(54) MULTI-WAVELENGTH PHYSIOLOGICAL MONITOR

(71) Applicant: Cercacor Laboratories, Inc., Irvine, CA (US)

(72) Inventors: Marcelo M. Lamego, Irvine, CA (US); Mohamed Diab, Mission Viejo, CA (US); Walter M. Weber, Laguna Hills, CA (US); Ammar Al-Ali, Tustin, CA (US); Joe Kiani, Laguna Niguel, CA (US)

(73) Assignee: MASIMO CORPORATION, Irvine, CA (US)

( * ) Notice: Subject to any disclaimer, the term of this patent is extended or adjusted under 35 U.S.C. 154(b) by 360 days.

This patent is subject to a terminal disclaimer.

(21) Appl. No.: 13/862,266

(22) Filed: Apr. 12, 2013

(65) Prior Publication Data

US 2013/0338461 A1    Dec. 19, 2013

Related U.S. Application Data

(63) Continuation of application No. 12/045,309, filed on Mar. 10, 2008, now Pat. No. 8,423,106, which is a continuation of application No. 11/139,291, filed on May 27, 2005, now Pat. No. 7,343,186.

(60) Provisional application No. 60/586,069, filed on Jul. 7, 2004.

(51) Int. Cl.
*A61B 5/1455* (2006.01)
*A61B 5/00* (2006.01)
(Continued)

(52) U.S. Cl.
CPC .......... *A61B 5/14552* (2013.01); *A61B 5/0205* (2013.01); *A61B 5/1495* (2013.01);
(Continued)

(58) Field of Classification Search
CPC .. A61B 5/1455; A61B 5/14551; A61B 5/145; A61B 5/14552
USPC ......... 600/310, 322, 323, 336, 340, 473, 476; 356/41
See application file for complete search history.

(56) References Cited

U.S. PATENT DOCUMENTS 3,638,640 A   2/1972   Shaw
3,922,088 A   11/1975  Lubbers et al.
(Continued)

FOREIGN PATENT DOCUMENTS

EP   1 778 072   5/2007
JP   06-178767   6/1994
(Continued)

OTHER PUBLICATIONS

Jan. 25, 2011 Office Action for Japanese Patent Application No. 2007-520308 filed on Jun. 6, 2005.
(Continued)

*Primary Examiner* — Eric Winakur
*Assistant Examiner* — Chu Chuan (JJ) Liu
(74) *Attorney, Agent, or Firm* — Knobbe, Martens, Olson & Bear, LLP

(57) ABSTRACT

A physiological monitor for determining blood oxygen saturation of a medical patient includes a sensor, a signal processor and a display. The sensor includes at least three light emitting diodes. Each light emitting diode is adapted to emit light of a different wavelength. The sensor also includes a detector, where the detector is adapted to receive light from the three light emitting diodes after being attenuated by tissue. The detector generates an output signal based at least in part upon the received light. The signal processor determines blood oxygen saturation based at least upon the output signal, and the display provides an indication of the blood oxygen saturation.

18 Claims, 12 Drawing Sheets

$$r = \frac{\sum_{i=1}^{n} \alpha_i NP_i}{\sum_{i=1}^{n} \beta_i NP_i}$$

(51) Int. Cl.
  *G01N 21/31* (2006.01)
  *A61B 5/0205* (2006.01)
  *A61B 5/1495* (2006.01)
  *A61B 5/024* (2006.01)
  *G01N 21/35* (2014.01)
  *G01N 21/359* (2014.01)

(52) U.S. Cl.
  CPC .......... *A61B5/14551* (2013.01); *A61B 5/6826* (2013.01); *A61B 5/6838* (2013.01); *A61B 5/72* (2013.01); *G01N 21/314* (2013.01); *A61B 5/02416* (2013.01); *G01N 21/35* (2013.01); *G01N 21/359* (2013.01); *G01N 2201/0627* (2013.01); *G01N 2201/129* (2013.01)

(56) References Cited

U.S. PATENT DOCUMENTS

| | | |
|---|---|---|
| 4,114,604 A | 9/1978 | Shaw et al. |
| 4,623,248 A | 11/1986 | Sperinde |
| 4,714,341 A | 12/1987 | Hamaguri et al. |
| 4,854,699 A | 8/1989 | Edgar, Jr. |
| 4,913,150 A | 4/1990 | Cheung et al. |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,222,495 A | 6/1993 | Clarke et al. |
| 5,319,355 A | 6/1994 | Russek |
| 5,337,744 A | 8/1994 | Branigan |
| 5,341,805 A | 8/1994 | Stavridi et al. |
| 5,355,880 A | 10/1994 | Thomas et al. |
| D353,195 S | 12/1994 | Savage et al. |
| D353,196 S | 12/1994 | Savage et al. |
| 5,377,676 A | 1/1995 | Vari et al. |
| 5,413,100 A | 5/1995 | Barthelemy et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,632,273 A | 5/1997 | Suzuki |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| 5,720,284 A | 2/1998 | Aoyagi et al. |
| D393,830 S | 4/1998 | Tobler et al. |
| 5,743,262 A | 4/1998 | Lepper, Jr. et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,589 A | 6/1998 | Bernreuter |
| 5,782,756 A | 7/1998 | Mannheimer |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,163,715 A | 12/2000 | Larsen et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,047 B1 | 5/2001 | Malin et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |

(56) References Cited

U.S. PATENT DOCUMENTS

| | | |
|---|---|---|
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,681,128 B2 | 1/2004 | Steuer et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,711,425 B1 | 3/2004 | Reuss |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,842,635 B1 | 1/2005 | Parker |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Al et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty et al. |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |

(56) References Cited

U.S. PATENT DOCUMENTS

| | | | |
|---|---|---|---|
| 7,899,518 B2 | 3/2011 | Trepagnier et al. | |
| 7,904,132 B2 | 3/2011 | Weber et al. | |
| 7,909,772 B2 | 3/2011 | Popov et al. | |
| 7,910,875 B2 | 3/2011 | Al-Ali | |
| 8,423,106 B2 | 4/2013 | Lamego et al. | |
| 2003/0163032 A1* | 8/2003 | Terry | 600/322 |
| 2004/0116788 A1 | 6/2004 | Chernoguz et al. | |
| 2011/0237911 A1 | 9/2011 | Lamego et al. | |

FOREIGN PATENT DOCUMENTS

| | | |
|---|---|---|
| JP | A 07-255709 | 10/1995 |
| JP | A 08-322822 | 12/1996 |
| JP | 10-507118 | 7/1998 |
| JP | 11-506652 | 6/1999 |

OTHER PUBLICATIONS

Jan. 31, 2012 Office Action for Japanese Patent Application No. 2007-520308 filed on Jun. 6, 2005.
Apr. 2, 2013 Office Action for Japanese Patent Application No. 2007-520308 filed on Jun. 6, 2005.
Jul. 30, 2013 Decision of Refusal for Japanese Patent Application No. 2007-520308 filed on Jun. 6, 2005.
Jan. 28, 2011 Office Action for European Patent Application No. 05 756 364.5 filed on Jun. 6, 2005.
Jul. 12, 2012 Office Action for European Patent Application No. 05 756 364.5 filed on Jun. 6, 2005.
Oct. 10, 2006 International Search Report and Written Opinion for PCT Application No. PCT/US05/19757 filed on Jun. 6, 2005.
Sep. 21, 2010 Supplemental Search Report for European Patent Application No. 05 756 364.5 filed on Jun. 6, 2005.
US 5,857,432, 01/1999, Thomas et al. (withdrawn)

* cited by examiner

MULTI-WAVELENGTH PHYSIOLOGICAL MONITOR

RELATED APPLICATIONS

This application is a continuation of U.S. application Ser. No. 12/045,309, filed Mar. 10, 2008, which is a continuation of U.S. application Ser. No. 11/139,291, filed May 27, 2005, now U.S. Pat. No. 7,343,186, which claims priority from U.S. Provisional No. 60/586,069, filed Jul. 7, 2004, each of which is incorporated by reference herein.

BACKGROUND OF THE INVENTION

1. Field of the Invention

The present invention relates to the field of signal processing. More specifically, the present invention relates to the processing of measured signals which contain a primary signal portion and a secondary signal portion for the removal or derivation of either signal portion. The present invention is especially useful for physiological monitoring systems, including blood oxygen saturation measurement systems and oximeters.

2. Description of the Related Art

Blood oxygen saturation measurement systems, oximeters, and physiological monitors of the prior art generally utilize two different wavelengths of light to determine a patient's blood oxygen saturation level. In general, such systems provide two wavelengths of light to a target location on a patient's body. The systems then measure at least one signal indicative of the transmission or reflection of the two light wavelengths with respect to the tissue at the target location.

One such physiological monitor is taught by Diab et al. in U.S. Pat. No. 5,632,272, incorporated by reference in its entirety herein. One embodiment of Diab's physiological monitor provides light having a red wavelength and light having an infrared wavelength to one side of a patient's finger. A detector on the opposite side of the patient's finger measures the red and infrared wavelength light transmitted through the patient's finger and generates a measurement signal. A processor analyzes the measurement signal to determine red and infrared component signals. Possible saturation values are input to a saturation equation module which provides reference coefficients. The red or infrared component signal is processed with the reference coefficients to yield reference signal vectors.

The reference signal vectors and the red or infrared component signal are processed by a correlation canceller to generate output vectors. The output vectors are input into a master power curve module, which provides a blood oxygen saturation value for each possible saturation value input to the saturation equation module. The patient's blood oxygen saturation is determined based upon the power curve module output.

DETAILED DESCRIPTION OF THE PREFERRED EMBODIMENT

Figure 1:
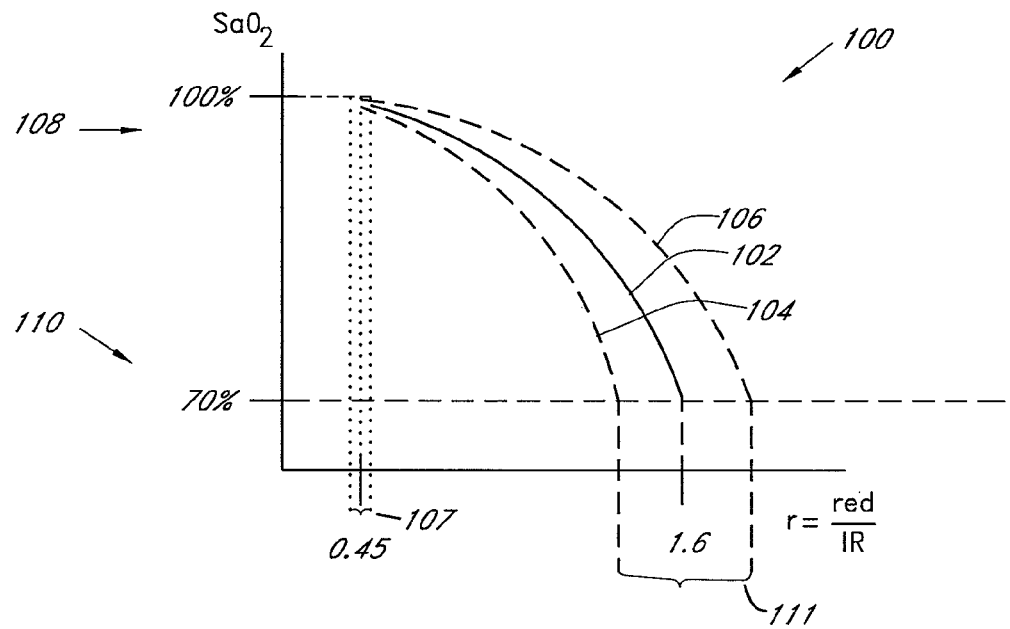
FIG. 1 illustrates an arterial blood oxygen saturation curve in accordance with the prior art.

A multi-wavelength physiological monitor in accordance with one embodiment of the present invention determines blood oxygen saturation by propagating multi-wavelength energy through a medium, such as a portion of a patient's body where blood flows close to the body surface. For example, in one embodiment, energy is propagated through an ear lobe, a digit (such as a finger or toe), a forehead, or a scalp (such as a fetus's scalp). An attenuated signal is measured after energy propagation through, or reflection from the medium. The physiological monitor determines the saturation of oxygenated blood in the patient based at least in part upon the measured signal.

It is well known by those of skill in the art that freshly oxygenated blood is pumped at high pressure from the heart into the arteries for use by the body. The volume of blood in the arteries varies with the heartbeat. This variation gives rise to a variation in energy absorption at the heartbeat rate, or the pulse.

Oxygen depleted, or deoxygenated, blood is returned to the heart through the veins with unused oxygenated blood. Unlike the arteries, the volume of blood in the veins varies with the rate of breathing, which is typically much slower than the heartbeat. Since the blood pressure in the veins is typically much lower than that of the arteries, the volume of blood in the veins varies in response to motion, such as a patient raising or lowering her arm. Changes in blood volume within the veins cause changes in vein thicknesses. Therefore, when there is no motion induced variation in the thickness of the veins, venous blood causes a low frequency variation in energy absorption, which is related to the rate of breathing. However, when erratic, motion-induced variations in the thickness of the veins occur, the low frequency variation in absorption is coupled with an erratic variation in energy absorption due to the erratic motion.

In one embodiment, absorption measurements are based upon the transmission of energy through a medium. In one embodiment, multiple light emitting diodes (LEDs) are positioned on one side of a portion of the body where blood flows close to the body's surface, such as a finger, and a photodetector is positioned on the opposite side of the surface. In another embodiment one or more such LEDs emit light of different wavelengths. In one embodiment, one LED emits a visible wavelength, such as red, and the other LED emits an infrared wavelength. However, one skilled in the art will realize that other wavelength combinations could be used.

The finger comprises skin, tissue, muscle, both arterial blood and venous blood, fat, etc., each of which absorbs light energy differently due to different absorption coefficients, different concentrations, different thicknesses, and changing optical pathlengths. When the patient is not moving, absorption is substantially constant except for variations due to the flow of blood through the skin, tissue, muscle, etc. A constant attenuation can be determined and subtracted from the measured signal via traditional filtering techniques. However, when the patient moves, perturbations such as changing optical pathlengths occur. Such perturbations may be due to movement of background fluids, (such as venous blood, which has a different saturation than arterial blood). Therefore, the measured signal becomes erratic. Erratic, motion-induced noise typically cannot be predetermined and subtracted from the measured signal via traditional filtering techniques. Thus, determining the oxygen saturation of arterial blood and venous in erratic, motion-induced noise environments, blood becomes more difficult.

In one embodiment, a physiological monitor measures light transmission through a patient's finger to determine arterial blood oxygen saturation. In some cases, however, the measured light signal contains noise, or other secondary signal, due to an event, such as patient movement during signal measurement. In such case, the signal measured by the physiological monitor includes a primary portion, related to the blood oxygen saturation of the patient, and a secondary portion, related to the noisy, erratic, motion-induced secondary signal. The physiological monitor processes the measured signal to determine the patient's blood oxygen saturation based upon the signal's primary portion.

In one embodiment, the physiological monitor utilizes a processor to determine a secondary reference signal n'(t) or $N_{ref}$. The secondary reference signal n'(t) is used to determine the primary portion of the measured signal. In one embodiment, the secondary reference signal n'(t) is input to a multi-variate process estimator, which removes the erratic, motion-induced secondary signal portions from the measured signal. In another embodiment, the processor determines a primary signal reference signal s'(t) which is used for display purposes or for input to a multi-variate process estimator to derive information about patient movement and venous blood oxygen saturation.

FIG. 1 illustrates an arterial blood oxygen saturation curve 100 representative of the sensitivity of blood oxygen saturation systems of the prior art. Such systems utilize two different wavelengths of light (such as red and infrared wavelength light) to determine blood oxygen saturation. Arterial blood oxygen saturation ($SaO_2$) is represented on the y-axis of the curve 100. The x-axis represents ratios of a red wavelength light transmission signal and an infrared wavelength light transmission signal.

An ideal saturation curve 102 would be highly accurate at all values. However, due to the limitations of using only two wavelengths of light, such systems typically operate between a lower range curve 104 and an upper range curve 106. Such blood oxygen saturation systems typically exhibit highly accurate, low tolerance 107 measurements at high saturation values 108, but at lower saturation values 110, that accuracy decreases, and increased tolerance 111 results.

Figure 2:
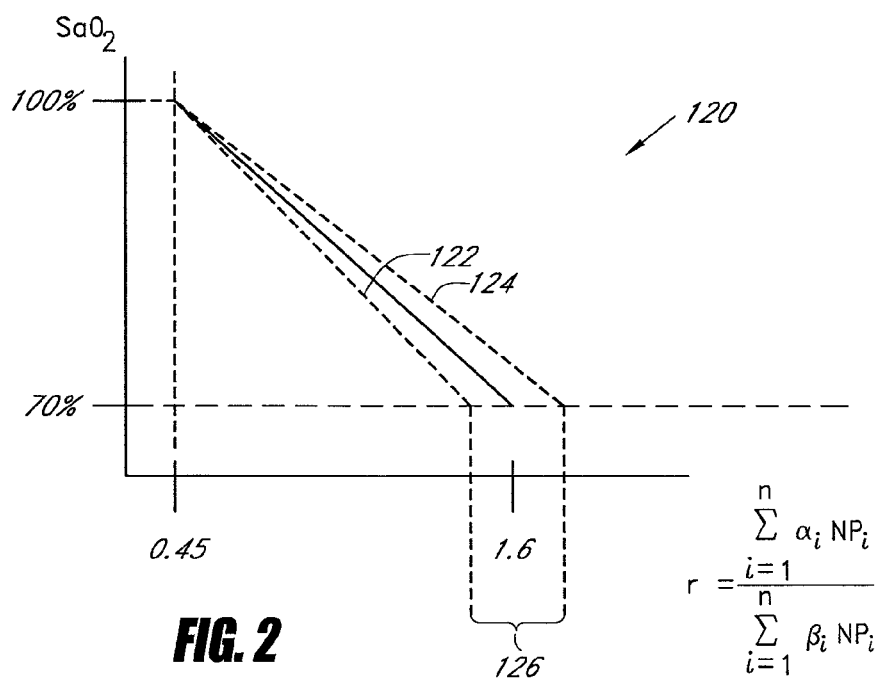
FIG. 2 illustrates an arterial blood oxygen saturation curve of a multi-wavelength physiological monitor in accordance with one embodiment of the present invention.

The arterial blood oxygen saturation curve 120 of a multi-wavelength physiological monitor in accordance with one embodiment of the present invention is shown in FIG. 2. The multi-wavelength system utilizes at least three different wavelengths of light ($\lambda_1, \lambda_2, \ldots \lambda_n$) to determine blood oxygen saturation. Arterial blood oxygen saturation ($SaO_2$) is represented on the y-axis of the curve 120. The x-axis represents ratios of composite signals, each comprising signals based upon the light transmission of the various light wavelengths ($\lambda_1, \lambda_2, \ldots \lambda_n$). Each ratio r can be express by:

$$r = \frac{\sum_{i=1}^{n} \alpha_i NP_{RMS,i}}{\sum_{i=1}^{n} \beta_i NP_{RMS,i}}$$

where n is the number of wavelengths of light utilized by the multi-wavelength physiological monitor, $NP_{RMS,i}$ is the normalized plethysmographic waveform of the $i^{th}$ wavelength light source, and $\alpha_i$ and $\beta_i$ are vector coefficients of known constants that are determined based upon fitting and/or calibration using experimental data and/or model(s).

The curve 120 contains lower and upper limit range curves 122, 124. However, the lower and upper limit range curves 122, 124 of the multi-wavelength physiological monitor are more linear than the lower and upper range curves 104, 106 of the dual-wavelength blood oximeter described above, as illustrated in FIG. 1. In addition, the lower and upper limit range curves 122, 124 of the multi-wavelength physiological monitor exhibit higher accuracy and lower tolerance 126 than the dual-wavelength blood oximeter of FIG. 1, particularly at lower arterial blood oxygen saturation levels. In certain cases, such as during the monitoring of neonates, or persons with low blood-oxygen saturation, it is desirable for the physiological monitor to exhibit increased accuracy at lower saturation levels. For example, when providing oxygen to a neonate, it is often critical that neither too much oxygen nor too little oxygen is provided.

Figure 3:
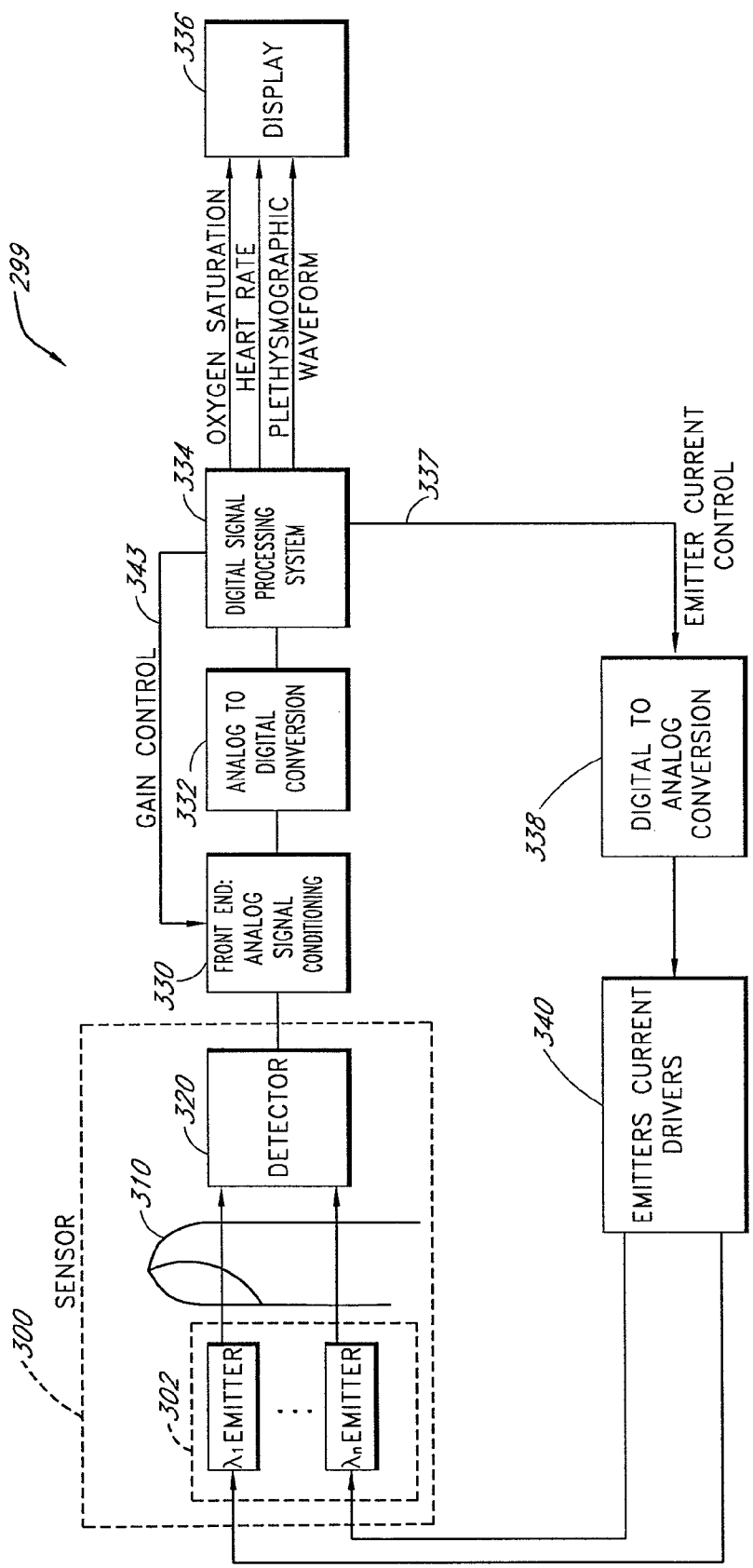
FIG. 3 is an example of a physiological monitor in accordance with one embodiment of the present invention.
Figure 4:
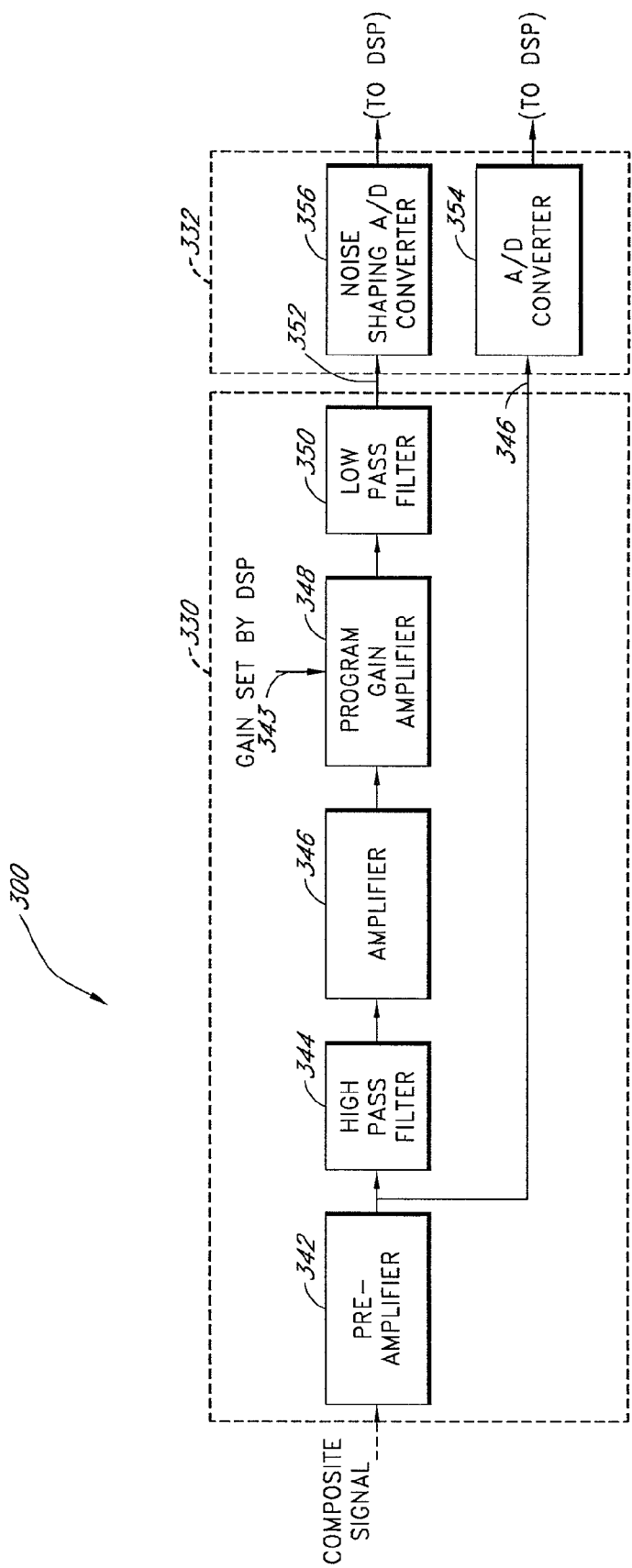
FIG. 4 illustrates one embodiment of the front end analog signal conditioning circuitry and the analog to digital conversion circuitry of the physiological monitor of FIG. 3.
Figure 5:
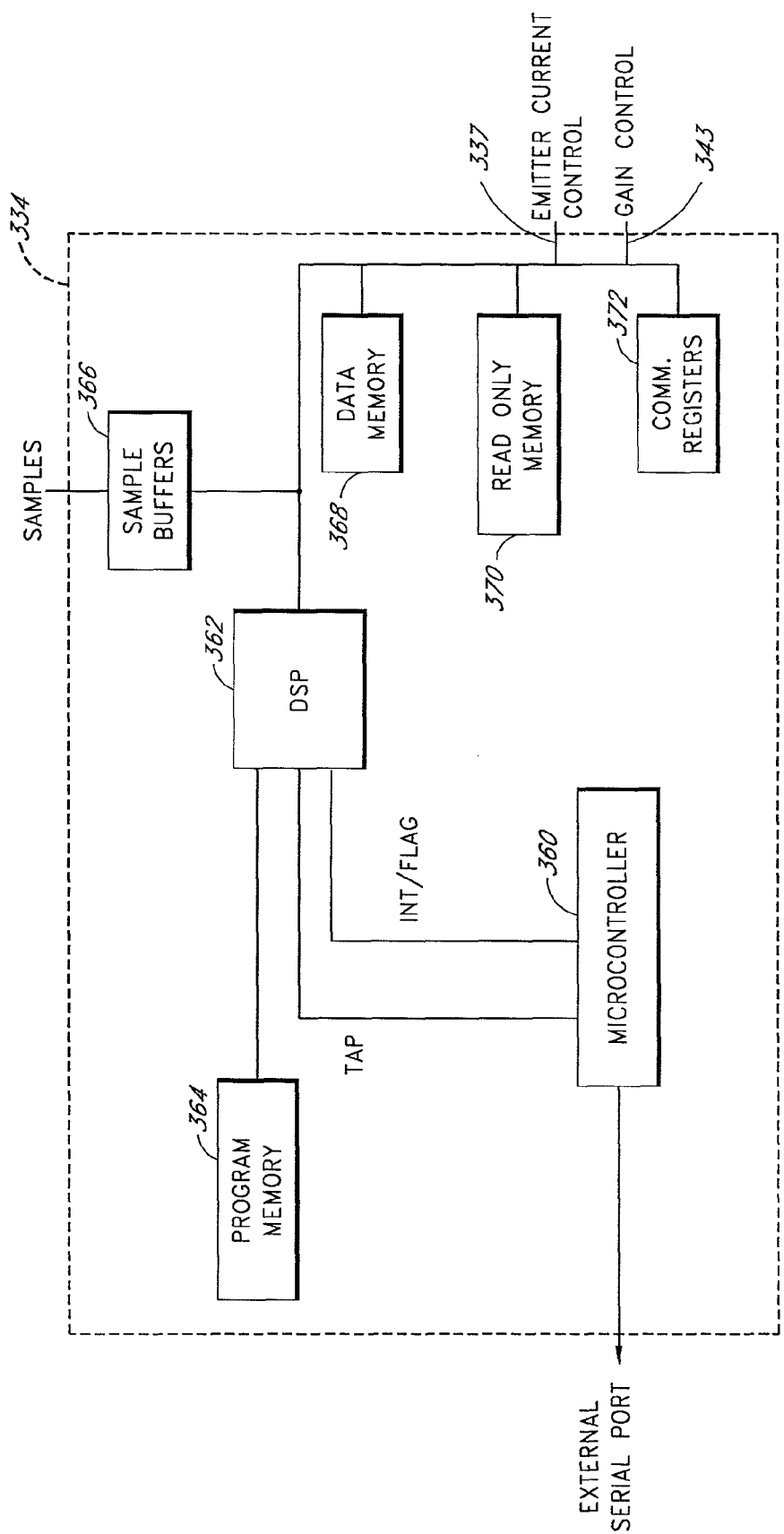
FIG. 5 illustrates one embodiment of the digital signal processing circuitry of FIG. 3.

A schematic of one embodiment of a multi-wavelength physiological monitor for pulse oximetry is shown in FIGS. 3-5. FIG. 3 depicts a general hardware block diagram of a multi-wavelength pulse oximeter 299. A sensor 300 has n LEDs 302, which in one embodiment are at least three light emitters. The n LEDs 302 emit light of different wavelengths ($\lambda_1, \lambda_2, \ldots \lambda_n$). In one embodiment, the n LEDs 302 include four, six, eight or sixteen LEDs of different wavelengths. In one embodiment, the n LEDs 302 are placed adjacent a finger 310. A photodetector 320 receives light from the n LEDs 302 after it has been attenuated by passing through the finger. The photodetector 320 produces at least one electrical signal corresponding to the received, attenuated light. In one embodiment, the photodetector 320 is located opposite the n LEDs 302 on the opposite side of the finger 310. The photodetector 320 is connected to front end analog signal conditioning circuitry 330.

The front end analog signal conditioning circuitry 330 has outputs that are coupled to an analog to digital conversion circuit 332. The analog to digital conversion circuit 332 has outputs that are coupled to a digital signal processing system 334. The digital signal processing system 334 provides desired parameters as outputs for a display 336. Outputs for the display 336 include, for example, blood oxygen saturation, heart rate, and a clean plethysmographic waveform.

The signal processing system also provides an emitter current control output 337 to a digital-to-analog converter circuit 338. The digital-to-analog converter circuit 338 provides control information to emitter current drivers 340. The emitter drivers 340 are coupled to the n light emitters 302. The digital signal processing system 334 also provides a gain control output 343 for front end analog signal conditioning circuitry 330.

Figure 3A:
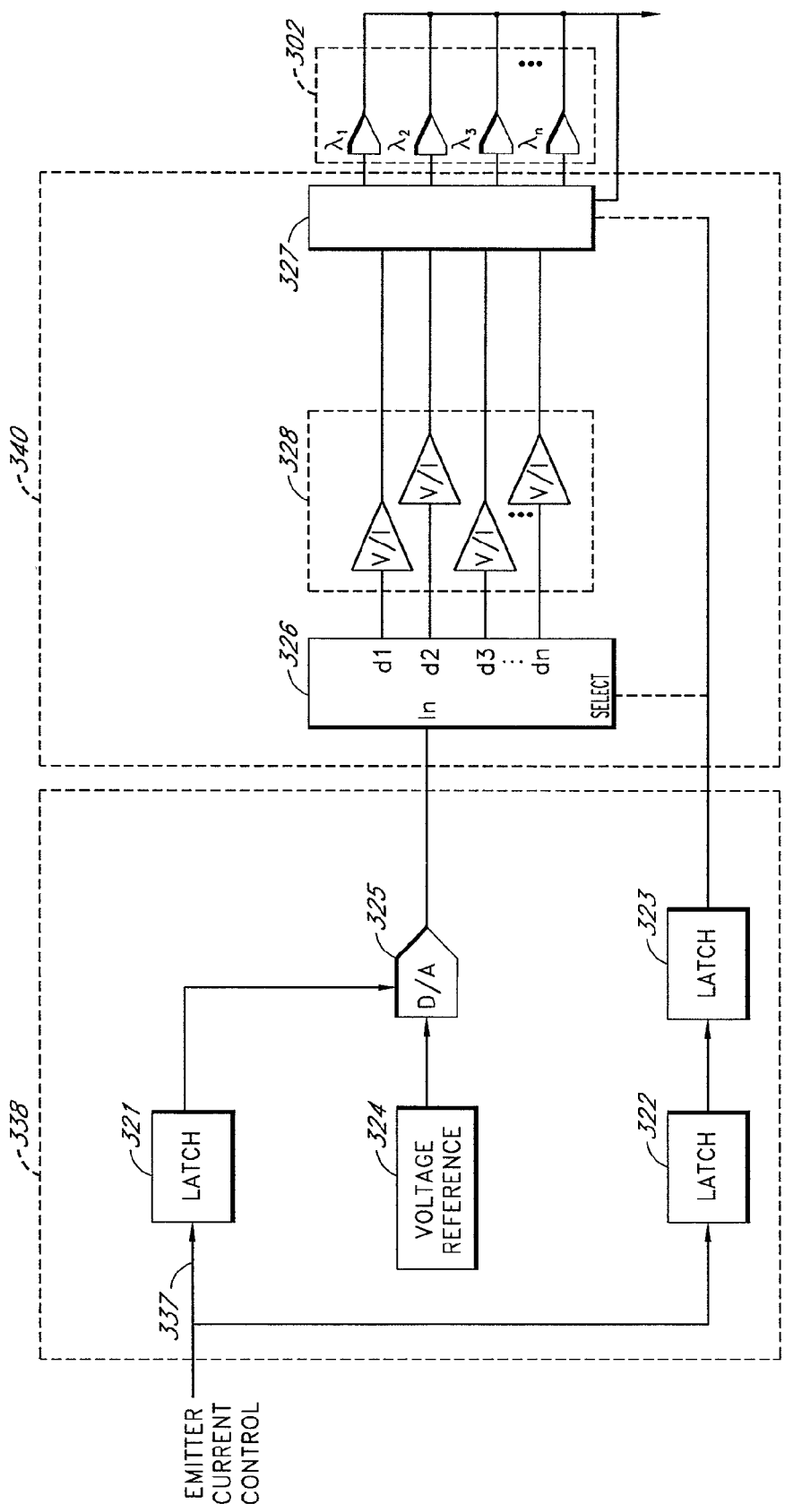
FIG. 3A illustrates one embodiment of the low noise emitter current driver of the physiological monitor of FIG. 3.

FIG. 3A illustrates one embodiment of the drivers 340 and the digital to analog conversion circuit 338. As depicted in FIG. 3A, the digital-to-analog conversion circuit 338 includes first and second input latches 321, 322, a synchronizing latch 323, a voltage reference 324, and a digital to analog conversion circuit 325. The emitter current drivers 340 include first and second switch banks 326, 327, and n voltage to current converters 328. LED emitters 302 of FIG. 3 are coupled to the output of the emitter current drives 340.

The driver depicted in FIG. 3A is advantageous in that the present inventors recognized that much of the noise in the oximeter 299 of FIG. 3 is caused by the LED emitters 302. Therefore, the emitter driver circuit of FIG. 3A is designed to minimize the noise from the emitters 302. The first and second input latches 321, 322 are connected directly to the DSP bus. Therefore, these latches significantly minimizes the bandwidth (resulting in noise) present on the DSP bus which passes through to the driver circuitry of FIG. 3A. The output of the first and second input latches only changes when these latched detect their address on the DSP bus. The first input latch 321 receives the setting for the digital to analog converter circuit 325. The second input latch 322 receives switching control data for the switch banks 326, 327. The synchronizing latch 323 accepts the synchronizing pulses which maintain synchronization between the activation of emitters 302 and the analog to digital conversion circuit 332.

The voltage reference is chosen as a low noise DC voltage reference for the digital to analog conversion circuit 325. In addition, in the present embodiment, the voltage reference has a lowpass output filter with a very low corner frequency (e.g., 1 Hz in the present embodiment). The digital to analog converter 325 also has a lowpass filter at its output with a very low corner frequency (e.g., 1 Hz). The digital to analog converter provides signals used to drive each of the emitters 302.

In the present embodiment, the output of the voltage to current converters 328 are switched such that, only one emitter is active at any given time. In addition, the voltage to current converter for the inactive emitter is switched off at its input as well, such that it is deactivated. This reduces noise from the switching and voltage to current conversion circuitry. In the present embodiment, low noise voltage to current converters 328 are selected (e.g., Op 27 Op Amps), and the feedback loop is configured to have a low pass filter to reduce noise. In the present embodiment, the low pass filtering function of the voltage to current converters 328 has a corner frequency of just above 625 Hz, which is the switching speed for the emitters 302, as further discussed below. Accordingly, the driver circuit embodiment of FIG. 3A, minimizes the noise of the emitters 302.

In general, the n light emitters 302 each emit light energy of a different wavelength, which is absorbed by the finger 310 and received by the photodetector 320. The photodetector 320 produces an electrical signal which corresponds to the intensity of the light energy striking the photodetector 320. The front end analog signal conditioning circuitry 330 receives the intensity signals and filters and conditions these signals as further described below for further processing. The resultant signals are provided to the analog-to-digital conversion circuitry 332, which converts the analog signals to digital signals for further processing by the digital signal processing system 334. The digital signal processing system 334 utilizes the signals in order to provide a what will be called herein a "saturation transform." It should be understood, that for parameters other than blood saturation monitoring, the saturation transform could be referred to as a concentration transform, in-vivo transform, or the like, depending on the desired parameter. The term "saturation transform" is used to describe an operation which converts the sample data from time domain to saturation domain values, as will be apparent from the discussion below. In the present embodiment, the output of the digital signal processing system 334 provides clean plethysmographic waveforms of the detected signals and provides values for oxygen saturation and pulse rate to the display 336.

It should be understood that in different embodiments of the present invention, one or more of the outputs may be provided. The digital signal processing system 334 also provides control for driving the n light emitters 302 with an emitter current control signal on the emitter current control output 337. This value is a digital value which is converted by the digital-to-analog conversion circuit 338, which provides a control signal to the emitter current drivers 340. The emitter current drivers 340 provide the appropriate current drive for the n light emitters 302. Further detail of the operation of the multi-wavelength physiological monitor for pulse oximetry is explained below.

In the present embodiment, the n light emitters 302 are driven via the emitter current driver 340 to provide light transmission with digital modulation at 625 Hz. In the present embodiment, the n light emitters 302 are driven at a power level that provides an acceptable intensity for detection by the detector 320 and for conditioning by the front end analog signal conditioning circuitry 330. Once this energy level is determined for a given patient by the digital signal processing system 334, the current level for the n light emitters 302 is maintained substantially constant. It should be understood, however, that the current could be adjusted for changes in the ambient room light and other changes that would affect the voltage input to the front end analog signal conditioning circuitry 330.

In one embodiment, the n light emitters 302 are modulated as follows: for one complete 625 Hz cycle, each emitter 302 is activated for one $1/2n$ cycle, and off for the remaining $(2n-1)/2n$ cycle. In order to only receive one signal at a time 302, the emitters are cycled on and off alternatively, in sequence, with each only active for a $1/2n$ cycle per 625 Hz cycle, with a $1/2n$ cycle separating the active times. The light signal is attenuated (e.g., amplitude modulated) by the pumping of blood through the finger 310 (or other sample medium). The attenuated (e.g., amplitude modulated) signal is detected by the photodetector 320 at the 625 Hz carrier frequency for the multi-wavelength light. Because only a single photodetector 320 is used, the photodetector 320 receives all light wavelength signals to form a composite time division signal.

The composite time division signal is provided to the front analog signal conditioning circuitry 330. Additional detail regarding the front end analog signal conditioning circuitry 330 and the analog to digital converter circuit 332 is illustrated in FIG. 4. As depicted in FIG. 4, in one embodiment, the front end circuitry 330 has a preamplifier 342, a high pass filter 344, an amplifier 346, a programmable gain amplifier 348, and a low pass filter 350. In one embodiment, the preamplifier 342 is a transimpedance amplifier that converts the composite current signal from the photodetector 320 to a corresponding voltage signal, and amplifies the signal. In the present embodiment, the preamplifier has a predetermined gain to boost the signal amplitude for ease of processing. In the present embodiment, the source voltages for the preamplifier 342 are −15 VDC and +15 VDC. As will be understood, the attenuated signal contains a component representing ambient light as well as a component representing the each of the multi-wavelengths of light over time. If there is light in the vicinity of the sensor 300 other than the multi-wavelengths of light from the n light emitters 302, this ambient light is detected by the photodetector 320. Accordingly, the gain of the preamplifier is selected in order to prevent the ambient light in the signal from saturating the preamplifier under normal and reasonable operating conditions.

In one embodiment, the preamplifier 342 includes an Analog Devices AD743JR OpAmp. This transimpedance amplifier is particularly advantageous in that it exhibits several desired features for the system described, such as: low equivalent input voltage noise, low equivalent input current noise, low input bias current, high gain bandwidth product, low total harmonic distortion, high common mode rejection, high open loop gain, and a high power supply rejection ratio.

The output of the preamplifier 342 is coupled to an input of the high pass filter 344. The output of the preamplifier also provides a first input 346 to the analog to digital conversion circuit 332. In the present embodiment, the high pass filter is a single-pole filter with a corner frequency of about ½-1 Hz. However, the corner frequency is readily raised to about 90 Hz in one embodiment. As will be understood, the 625 Hz carrier frequency of the multi-wavelength light signal is well above a 90 Hz corner frequency. The high-pass filter 344 has an output coupled as an input to an amplifier 346. In the present embodiment, the amplifier 346 comprises a unity gain amplifier. However, the gain of the amplifier 346 is adjustable by the variation of a single resistor. The gain of the amplifier 346 is increased if the gain of the preamplifier 342 is decreased to compensate for the effects of ambient light.

The output of the amplifier 346 provides an input to a programmable gain amplifier 348. The programmable gain amplifier 348 also accepts a programming input from the digital signal processing system 334 on a gain control signal line 343. In one embodiment, the gain of the programmable gain amplifier 348 is digitally programmable. The gain is adjusted dynamically at initialization or at sensor placement due to changes in the medium (e.g., the finger) and due to variations in the medium from patient to patient. Therefore, a dynamically adjustable amplifier is provided by the programmable gain amplifier 348 in order to obtain a signal suitable for processing.

The programmable gain amplifier 348 is also advantageous in an alternative embodiment in which the emitter drive current is held constant. In the present embodiment, the emitter drive current is adjusted for each patient in order to obtain the proper dynamic range at the input of the analog to digital conversion circuit 332. However, changing the emitter drive current can alter the emitter wavelength, which in turn affects the end result in oximetry calculations. Accordingly, in another embodiment, it is advantageous to fix the emitter drive current for all patients. In an alternative embodiment of the present invention, the programmable gain amplifier can be adjusted by the DSP in order to obtain a signal at the input to the analog to digital conversion circuit which is properly within the dynamic range (+3 V to −3 V in the present embodiment) of the analog to digital conversion circuit 332. In this manner, the emitter drive current could be fixed for all patients, eliminating wavelength shift due to emitter current drive changes.

The output of the programmable gain amplifier 348 couples as an input to a low-pass filter 350. Advantageously, the low pass filter 350 is a single-pole filter with a corner frequency of approximately 10 kHz in the present embodiment. This low pass filter provides anti-aliasing in the present embodiment.

The output of the low-pass filter 350 provides a second input 352 to the analog-to-digital conversion circuit 332. In the present embodiment, the analog-to-digital conversion circuit 332 comprises a first analog-to-digital converter 354 and a second analog-to-digital converter 356. Advantageously, the first analog-to-digital converter 354 accepts input from the first input 346 to the analog-to-digital conversion circuit 332, and the second analog to digital converter 356 accepts input on the second input 352 to the analog-to-digital conversion circuitry 332.

In one embodiment, the first analog-to-digital converter 354 is a diagnostic analog-to-digital converter. The diagnostic task (performed by the digital signal processing system) is to read the output of the detector as amplified by the preamplifier 342 in order to determine if the signal is saturating the input to the high-pass filter 344. In the present embodiment, if the input to the high pass filter 344 becomes saturated, the front end analog signal conditioning circuits 330 provides a "0" output. Alternatively, in another embodiment, a first analog-to-digital converter 354 is not used.

The second analog-to-digital converter 356 accepts the conditioned composite analog signal from the front end signal conditioning circuitry 330 and converts the signal to digital form. In the present embodiment, the second analog to digital converter 356 comprises a single-channel, delta-sigma converter. In the present embodiment, a Crystal Semiconductor CS5317-KS delta-sigma analog to digital converter is used. Such a converter is advantageous in that it is low cost and exhibits low noise characteristics. More specifically, a delta-sigma converter consists of two major portions: a noise modulator and a decimation filter. The selected converter uses a second order analog delta-sigma modulator to provide noise shaping. Noise shaping refers to changing the noise spectrum from a flat response to a response where noise at the lower frequencies has been reduced by increasing noise at higher frequencies. The decimation filter then cuts out the reshaped, higher frequency noise to provide 16-bit performance at a lower frequency. The present converter samples the data 128 times for every 16 bit data word that it produces. In this manner, the converter provides excellent noise rejection, dynamic range and low harmonic distortion, that help in critical measurement situations like low perfusion and electrocautery.

In addition, by using a single-channel converter, there is no need to tune two or more channels to each other. The delta-sigma converter is also advantageous in that it exhibits noise shaping, for improved noise control. An exemplary analog to digital converter is a Crystal Semiconductor CS5317. In the present embodiment, the second analog to digital converter 356 samples the signal at a 20 kHz sample rate. The output of the second analog to digital converter 356 provides data samples at 20 kHz to the digital signal processing system 334 (FIG. 3).

The digital signal processing system 334 is illustrated in additional detail in FIG. 5. In the present embodiment, the digital signal processing system includes a microcontroller 360, a digital signal processor (DSP) 362, a program memory 364, a sample buffer 366, a data memory 368, a read only memory 370 and communication registers 372. In one embodiment, the digital signal processor 362 is an Analog Devices AD 21020, although other digital signal processors may be employed, as is well known by those of skill in the art. In one embodiment, the microcontroller 360 comprises a Motorola 68HC05, with built in program memory. In the present embodiment, the sample buffer 366 is a buffer which accepts the 20 kHz sample data from the analog to digital conversion circuit 332 for storage in the data memory 368. In the present embodiment, the data memory 368 comprises 32 kWords (words being 40 bits in the present embodiment) of static random access memory. Other chips, data rates and data memory configurations may be employed, as is well known to those of skill in the art.

In one embodiment, the microcontroller 360 is coupled to the DSP 362 via a conventional JTAG Tap line. The microcontroller 360 transmits the boot loader for the DSP 362 to the program memory 364 via the Tap line, and then allows the DSP 362 to boot from the program memory 364. The boot loader in program memory 364 then causes the transfer of the operating instructions for the DSP 362 from the read only memory 370 to the program memory 364. Advantageously, the program memory 364 is a very high speed memory for the DSP 362. The microcontroller 360 provides the emitter current control and gain control signals via the communications register 372.

Figure 6:
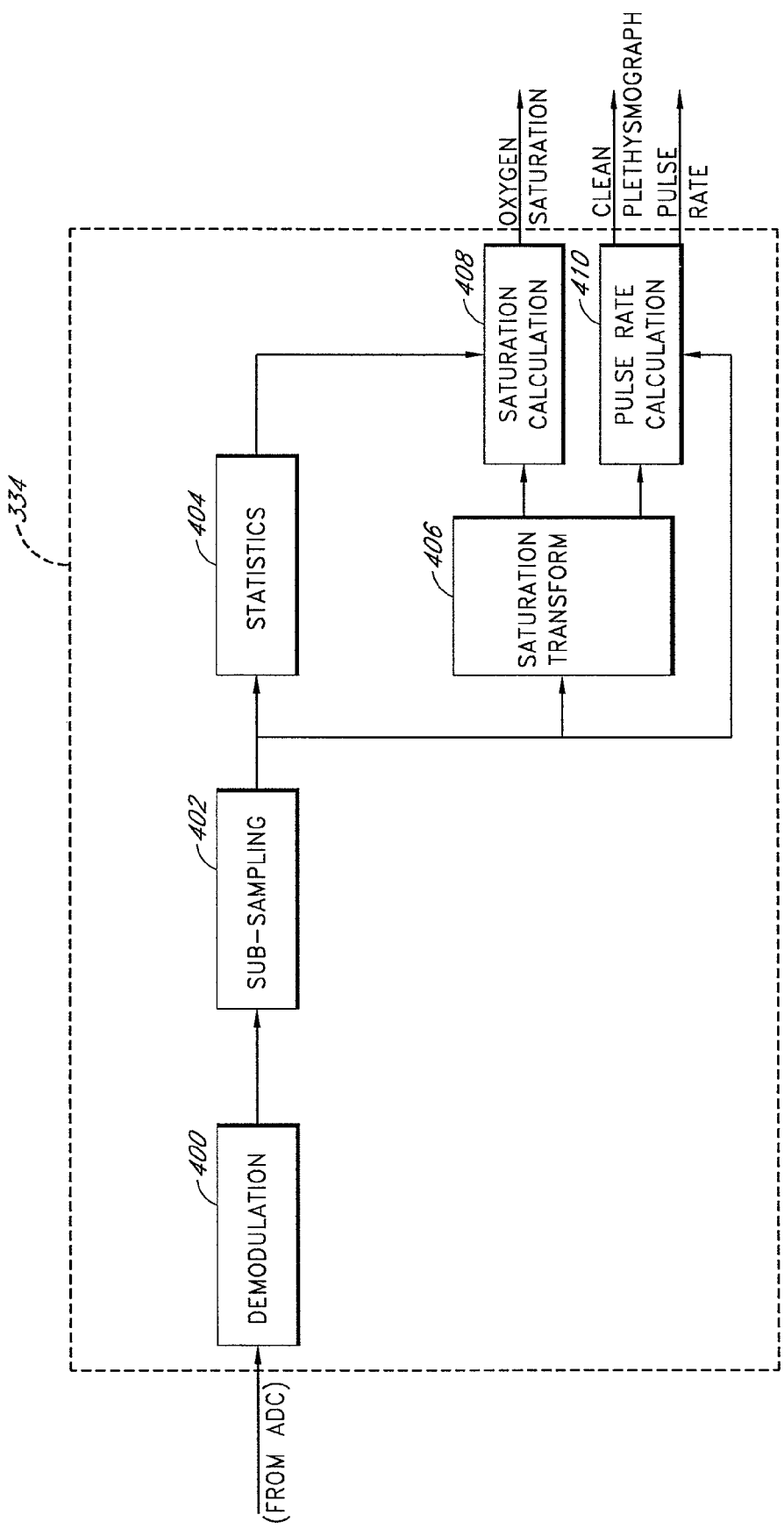
FIG. 6 illustrates one embodiment of additional operations performed by the digital signal processing circuitry of FIG. 3.

FIGS. 6-10 depict functional block diagrams of the operations of the multi-wavelength pulse oximeter 299 that in one embodiment are executed by the digital signal processing system 334. The signal processing functions described below are carried out by the DSP 362 in the present embodiment, with the microcontroller 360 providing system management. In the present embodiment, the operation is software/firmware controlled. FIG. 6 depicts a generalized functional block diagram for the operations performed on the 20 kHz sample data entering the digital signal processing system 334. As illustrated in FIG. 6, a demodulation operation, as represented in a demodulation module 400, is first performed. Sub-sampling, as represented by sub-sampling operation 402, is then performed on the resulting data. Certain statistics are calculated, as represented in a statistics module 404. A saturation transform is performed, as represented in a saturation transform module 406, on the data resulting from the sub-sampling operation 402. The data subjected to the statistics operations and the data subjected to the saturation transform operations are forwarded to saturation operations, as represented by a saturation calculation module 408 and pulse rate operations, as represented by pulse rate calculation module 410.

In general, the demodulation operation separates each of the multi-wavelength signals from the composite signal and removes the carrier frequency, leaving raw data points. The raw data points are provided at intervals (e.g., at 625 Hz) to the sub-sampling operation 402, which in one embodiment, reduces the samples by an order of 10 from samples at 625 Hz to samples at 62.5 Hz. The sub-sampling operation also provides some filtering on the samples. The resulting data is subjected to statistics and saturation transform operations 404, 406 to calculate a saturation value, which is very tolerant to motion artifacts and other noise in the signal. The saturation value is ascertained in the saturation calculation module 408, and a pulse rate and a clean plethysmographic waveform are obtained through the pulse rate module 410. Additional details regarding the various operations are provided in connection with FIGS. 7-10.

Figure 7:
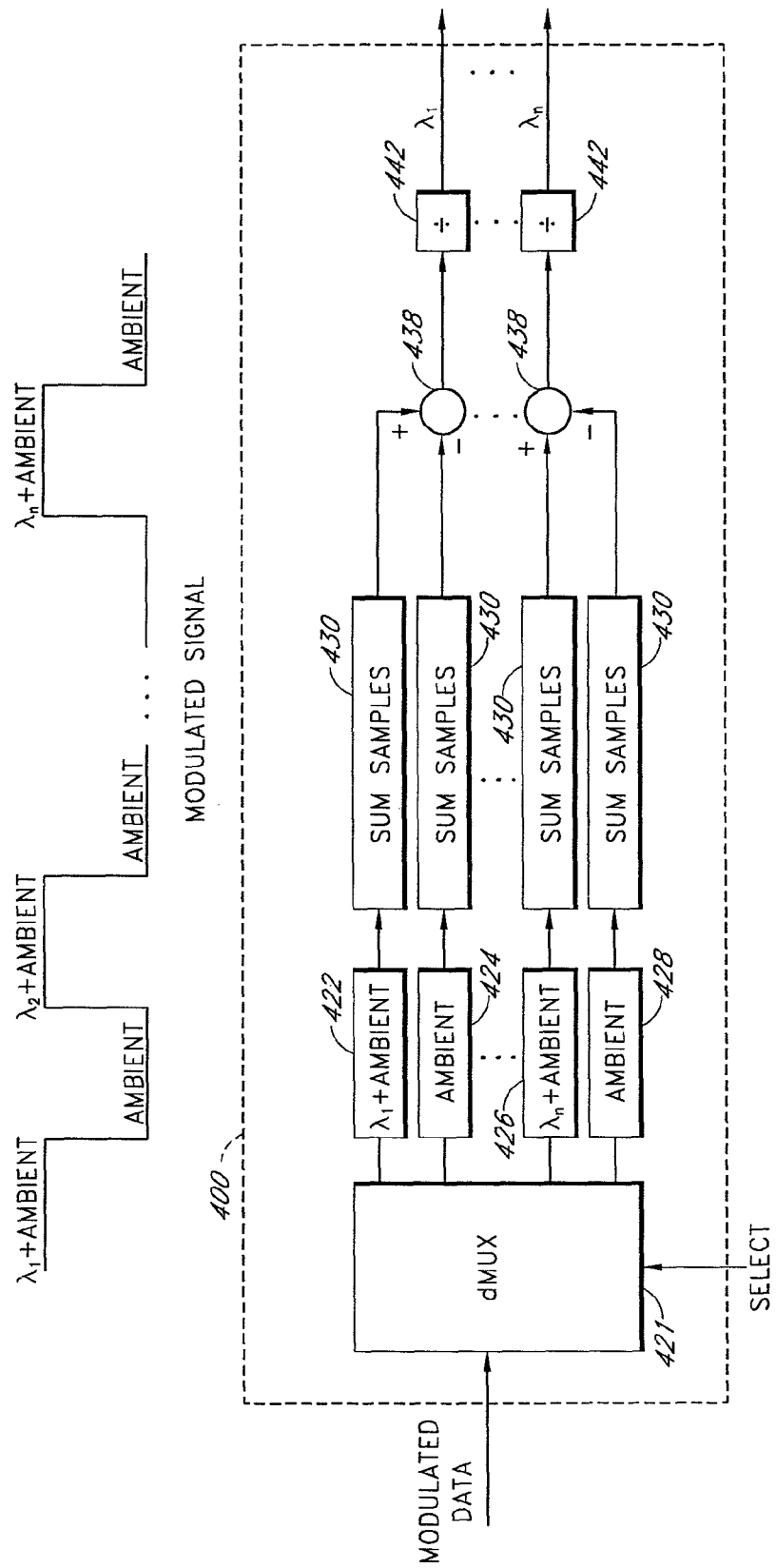
FIG. 7 illustrates one embodiment of the demodulation module of FIG. 6.

FIG. 7 illustrates one embodiment of the operation of the demodulation module 400. One embodiment of a composite, modulated signal format is depicted in FIG. 7. One full 625 Hz cycle of the n-wavelength, composite signal is depicted in FIG. 7 with the first ½n cycle including the first light wavelength signal plus ambient light signal, the second ½n cycle including an ambient light signal, the third ½n cycle including the second light wavelength signal plus ambient light signal, and the fourth ½n cycle including an ambient light signal. In one embodiment, this pattern repeats n times, wherein the $(2n-1)^{th}$ ½n cycle includes the $n^{th}$ light wavelength signal plus an ambient light signal, and the $2n^{th}$ cycle includes an ambient light signal.

Alternatively, in another embodiment, the first cycle of the composite signal includes the first light wavelength signal plus an ambient light signal, and the second cycle of the composite signal includes the second light wavelength signal plus an ambient light signal. This pattern repeats to the $n^{th}$ cycle of the composite signal, which includes the $n^{th}$ wavelength signal plus an ambient light signal. In such embodiment, the $(n+1)^{th}$ cycle includes only an ambient light signal.

As depicted in FIG. 7, when a 20 kHz sampling frequency is utilized, the single full cycle at 625 Hz described above comprises 32 samples of 20 kHz data, eight samples relating to the first wavelength of light plus ambient light, eight samples relating to ambient light, eight samples relating to the second wavelength of light plus ambient light, finally eight samples related to ambient light, etc. This pattern repeats for each of the n wavelength of light.

Because the signal processing system 334 controls the activation of the light emitters 302, the entire system is synchronous. In one embodiment, the data is synchronously divided (and thereby demodulated) into 2n 8-sample packets, with a time division demultiplexing operation as represented in a demultiplexing module 421. One eight-sample packet 422 represents the first wavelength of light plus ambient light signal, a second eight-sample packet 424 represents an ambient light signal, a third eight-sample packet (not shown) represents the attenuated second wavelength of light plus ambient light signal, a fourth eight-sample packet (not shown) represents the ambient light signal. This structure repeats until the $(2n-1)^{th}$ eight-sample packet 426, which represents the attenuated $n^{th}$ wavelength of light plus ambient light signal, and $2n^{th}$ eight-sample packet 428, which represents an ambient light signal. A select signal synchronously controls the demultiplexing operation so as to divide the time-division multiplexed composite signal at the input of the demultiplexer 421 into its n subparts.

In one embodiment, the last several samples from each packet are then processed as follows. A sum of the last four samples from each packet is calculated, as represented in the summing operations 430 of FIG. 7. In the present embodiment, the last four samples are used because a low pass filter in the analog to digital converter 356 of the present embodiment has a settling time. However, any number of samples may be so summed. The selection of the number of samples to be summed will be determined based at least in part on the settling time of the n LEDs 302 (not shown). Collecting the last four samples from each 8-sample packet allows the previous signal to clear. This summing operation provides an integration operation which enhances noise immunity. The sum of the respective ambient light samples is then subtracted from the sum of each of the individual wavelength samples, as represented in the subtraction modules 438. It should be understood that in one embodiment, for n wavelengths of light, there will be n subtraction modules 438. The subtraction operation provides some attenuation of the ambient light signal present in the data. In the present embodiment, it has been found that approximately 20 dB attenuation of the ambient light is provided by the operations of the subtraction modules 438. The resultant individual wavelength sum values are divided by the number of samples summed in summing operations 430. In the present embodiment, the sum values are divided by four, as represented in the divide modules 442. Each resultant value provides one sample each of each of the individual wavelengths light signals at 625 Hz.

It should be understood that the carrier frequency has been removed by the demodulation operation 400. In one embodiment, the 625 Hz sample data at the output of the demodulation operation 400 is sample data without the carrier frequency. In order to satisfy Nyquist sampling requirements, less than 20 Hz is used (understanding that the human pulse is about 25 to 250 beats per minute, or about 0.4 Hz-4 Hz). Accordingly, the 625 Hz resolution is reduced to 62.5 Hz in the sub-sampling operation 402 (not shown). Although in the present embodiment the sub-sampling operation 400 effectively reduces the data rate by 10:1, other such sub-sampling ratios may be used. The term "sub-sampling," in addition to its ordinary meaning, is intended to include decimation and sub-sampling at any appropriate rate or ratio. Such methods are well known to those of skill in the art.

Figure 8:
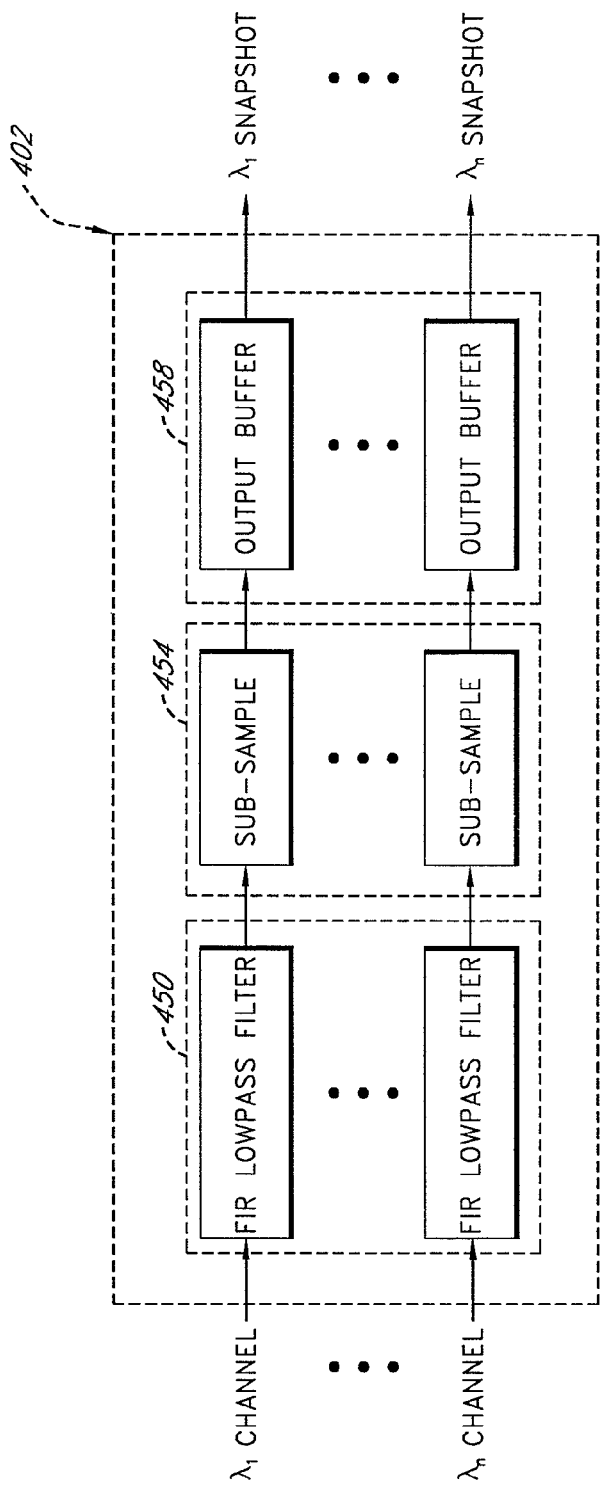
FIG. 8 illustrates one embodiment of the sub-sampling module of FIG. 6.

FIG. 8 illustrates the operations of one embodiment of the sub-sampling module 402 of FIG. 6. The multi-wavelength light sample data is provided at 625 Hz to corresponding buffers or filters 450. It should be understood that in one embodiment, for n wavelengths of light, there are n corresponding buffers or filters 450. In the present embodiment, the multi-wavelength light buffers/filters 450 are 519 samples deep, although other such buffers or filters may be used, as is well known to those of skill in the art. In one embodiment, the buffer filters 450 function as continuous first-in, first-out buffers (FIFO buffers). The 519 samples of each buffer filter 450 are subjected to low-pass filtering. Preferably, the low-pass filtering has a cutoff frequency of approximately 7.5 Hz with attenuation of approximately −110 dB. The buffer/filters 450 form a Finite Impulse Response (FIR) filter with coefficients for 519 taps. In order to reduce the sample frequency by ten, the low-pass filter calculation is performed every ten samples, as represented in sub-sample modules 454. In other words, with the transfer of each new ten samples into the buffer/filters 450 a new low pass filter calculation is performed by multiplying the impulse response (coefficients) by the 519 filter taps. Each filter calculation provides one output sample for respective output buffers 458. In the present embodiment, the output buffers 458 are also continuous FIFO buffers that hold 570 samples of data. The 570 samples provide respective samples or packets (also denoted "snapshot" herein) of samples. The output buffers 458 provide sample data to the statistics operation module 404, saturation transform module 406, and the pulse rate module 410, as illustrated in FIG. 6.

Figure 9:
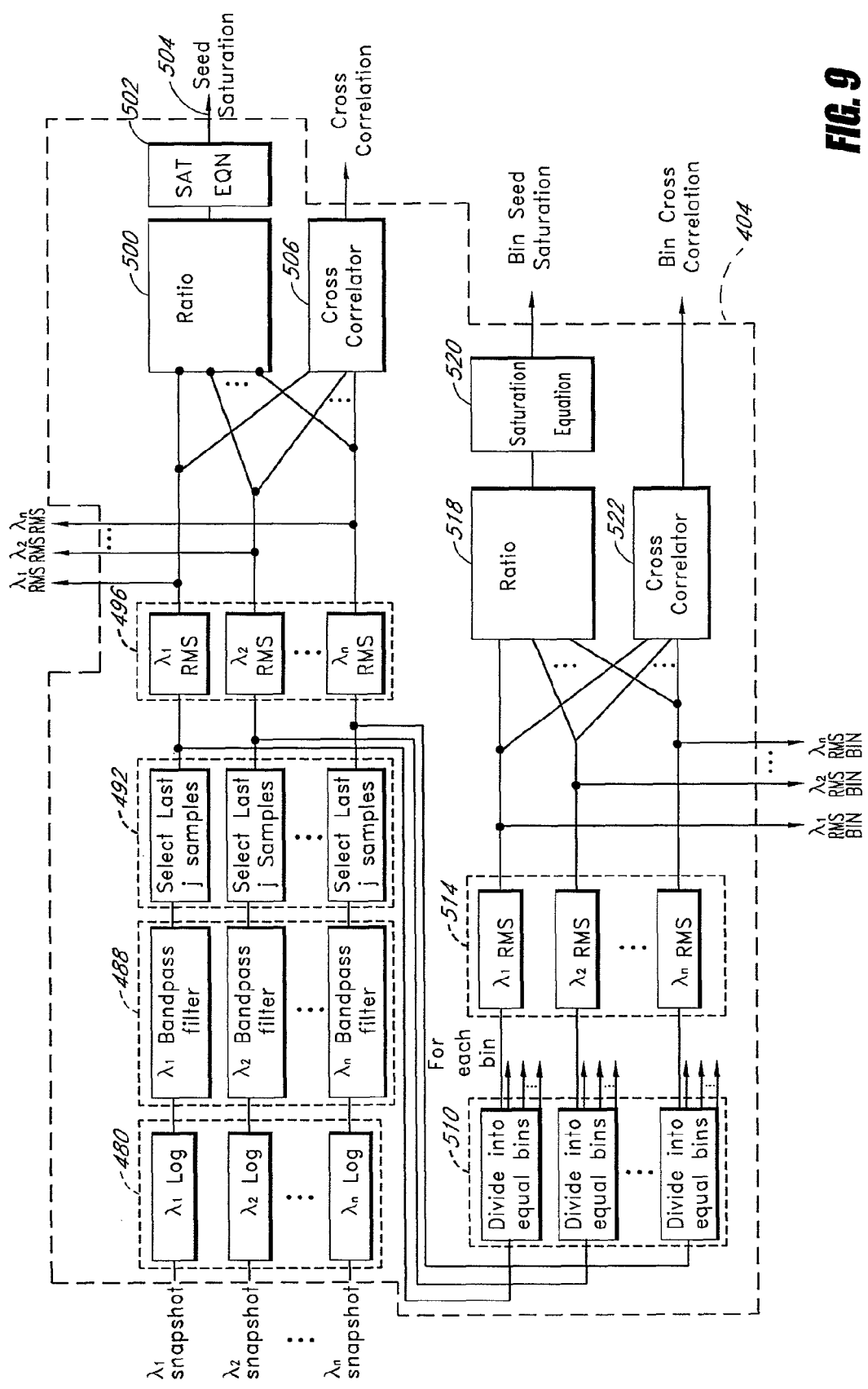
FIG. 9 illustrates one embodiment of the statistics module of FIG. 6.

FIG. 9 illustrates additional functional operation details of the statistics module 404. In summary, the statistics module 404 provides first order oximetry calculations and RMS signal values for each of the n wavelengths of light. The statistics module 404 also provides a cross-correlation output which indicates a cross-correlation between the n wavelengths of light.

As represented in FIG. 9, the statistics module 404 receives n packets of samples from the output buffers 458 (not shown) of the sub-sampling module 402 of FIGS. 6 and 8. In one embodiment, the samples include 570 samples at 62.5 Hz which represent the attenuated n wavelengths of light signals with the carrier frequency removed. Each packet is normalized with a log function, as represented in the n log modules 480.

The signals are then subjected to bandpass filtering, as represented in the n bandpass filter modules 488. In the present embodiment, with 570 samples in each packet, the bandpass filters are configured with 301 taps to provide a FIR filter with a linear phase response and little or no distortion. In the present embodiment, the bandpass filter has a pass band from 34 beats/minute to 250 beats/minute. The 301 taps slide over each 570 sample packet in order to obtain 270 filtered samples for each of the n filtered wavelength signal. In one embodiment, the n bandpass filters 488 remove the DC in the signal. However, in another embodiment, addition DC removal operations (not shown) may be provided to assist in DC removal.

After filtering, the last j samples from each packet (each packet now containing 270 samples in the present embodiment) are selected for further processing, as represented in the n select last j samples modules 492. In one embodiment, j equals 120, and the last 120 samples are selected in the select last j samples modules 492. In one embodiment, 120 samples are selected because the first 150 samples fall within the settling time for the saturation transfer module 406. The saturation transfer module 406 processes the same data packets, as further discussed below.

In the present embodiment, saturation equation calculations are performed on each 120-sample packet. In the present embodiment, the saturation calculations are performed in two different ways. For one calculation, the 120-sample packets are processed to obtain each packet's overall RMS value, as represented in the $\lambda_1$ through $\lambda_n$ RMS modules 496. It should be understood that in the present embodiment there are n such RMS modules, although as few as one RMS module may be used. The resultant RMS values for each of the n wavelengths of light provide input values to a first ratio operation 500, which provides its output as an input to a saturation equation module 502. The ratio operation 500 calculates a ratio of the various signals based upon the multi-wavelength model described above, and illustrated as:

$$r = \frac{\sum_{i=1}^{n} \alpha_i NP_{RMS,i}}{\sum_{i=1}^{n} \beta_i NP_{RMS,i}}$$

The ratio of the intensity of different light wavelengths may be used to determine the oxygen saturation of the patient. In one embodiment, the ratio is provided to a saturation equation module 502, which includes a look-up table, a polynomial, or the like. The saturation equation module 502 provides a saturation values at its output 504 based upon the ratio. In another embodiment, the n wavelengths's individual RMS values are also provided as outputs of the statistics operations module 404.

The n 120-sample packets (corresponding to each of the n wavelengths of light) are subjected to a cross-correlation operation as represented in a first cross-correlation module 506. The first cross-correlation module 506 determines if good correlation exists between the various light wavelength signals. This cross correlation is advantageous for detecting defective or otherwise malfunctioning detectors. The cross correlation is also advantageous in detecting when the signal model is satisfied. The signal model of the multi-wavelength physiological monitor is described in greater detail above with respect to FIG. 2, and in greater detail below, with respect to FIG. 10. If correlation becomes too low between the signals, the signal model is not satisfied. In order to determine whether the signal model is satisfied, the normalized cross correlation can be computed by the cross-correlation module 506 for each snapshot of data.

In one embodiment, correlation between any two wavelength signals $x_1$ and $x_2$ is determined according to:

$$\frac{\sum_j x_{1,j} x_{2,j}}{\sqrt{\sum_j x_{1,j}} \sqrt{\sum_j x_{2,j}}}$$

For n wavelengths, a cross-correlation matrix, Corr [x x$^T$], is determined, where x∈R$^n$. In one embodiment, a minimum value of the cross-correlation matrix is determined. The minimum value may be determined by looking for the minimum value within the matrix, or the minimum eigenvalue of the matrix. Other methods may be used, as are well known to those of skill in the art.

If the cross-correlation minimum value is too low, the oximeter 299 provides a warning (e.g., audible, visual, etc.) to the operator. In the present embodiment, if a selected snapshot yields a normalized correlation of less than 0.75, the snapshot does not qualify. Signals which satisfy the signal model will have a correlation greater than the threshold.

In one embodiment, the 120-sample packets are also subjected to a second saturation operation and cross correlation in the same manner as described above, except the 120-sample packets are first divided into equal bins of samples (e.g., five bins of 24 samples each). The RMS, ratio, saturation, and cross correlation operations are performed on a bin-by-bin basis. These operations are represented in the divide into equal bins modules 510 the second RMS modules 514 the second ratio module 518, the second saturation equation module 520, and the second cross-correlation module 522, as illustrated in FIG. 9. In one embodiment, the divide into equal bins modules 510 divide the data into five equal bins. However, the divide into equal bins modules 510 may divide the data into any desirable number of equal bins, for example, 7 bins, 10 bins or 20 bins.

Figure 10:
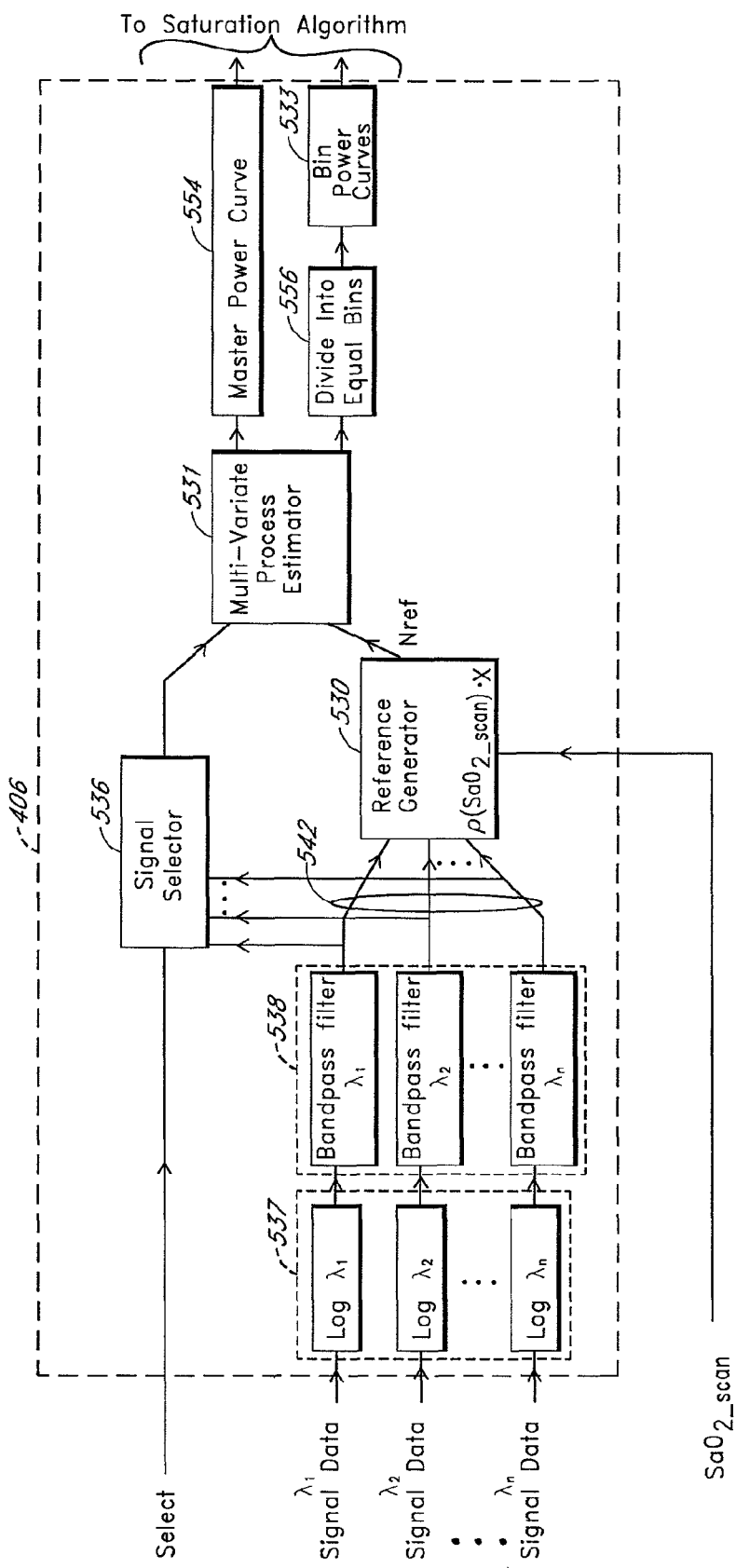
FIG. 10 illustrates a block diagram of the operations of one embodiment of the saturation transform module of FIG. 6.

FIG. 10 illustrates additional detail regarding the saturation transform module 406 of FIG. 6. As illustrated in FIG. 10, the saturation transform module 406 includes log module 537, bandpass filter module 538, signal selector module 536, reference generator 530, a multi-variate process estimator 531, a master power curve module 554, a divide into equal bins module 556, and a bin power curve module 533. In another embodiment, the saturation transform module has a reference processor, a correlation canceler, and an integrator to provide a power curve for separate signal coefficients. Reference processors, correlation cancelers, and integrators are well known to those of skill in the art, and are described in U.S. Pat. Nos. 5,632,272 and 5,490,505, both of which are incorporated by reference herein in their entireties.

As depicted in FIG. 10, the saturation transform module 406 receives the n packets (one packet for each wavelength of light) from the sub-sampling module 402 (not shown) of FIG. 6. In one embodiment, each of the n packets contains 570 samples, although other sized packets may be employed. The data stored in the n packets, indicated in FIG. 10 as $\lambda_1$ Signal Data, $\lambda_2$ Signal Data, ... $\lambda_n$, Signal Data, is processed by log module 537. Log module 537 performs a logarithmic function on each of the n packets, similar to the log module 480 of the statistics module 404 described above with reference to FIG. 9. The output of the log module 537 is input to a bandpass filter module 538. In one embodiment, the bandpass filter module 538 performs the same type of filtering as the n bandpass filters 488 of the statistics module 404 described above with reference to FIG. 9. Accordingly, each set of 570 samples subjected to bandpass filtering results in 270 remaining samples. The resulting data at the n outputs 542 of the bandpass filter module 538 are, in one embodiment, n vectors of 270 samples. Each output 542 represents the normalized plethysmographic waveform of the corresponding wavelength of light. The outputs 542 are provided to a signal selector module 536 and a reference generator 530.

A plurality of possible saturation values (the "saturation axis scan," or SaO$_{2\_scan}$ values) are provided to the saturation reference processor 530 in addition to the normalized plethysmographic waveform outputs 542. In the present embodiment, 117 saturation values are provided as the saturation axis scan. In a preferred embodiment, the 117 saturation values range uniformly from a blood oxygen saturation of 34.8 to 105.0. Accordingly, in the present embodiment, the 117 saturation values provide an axis scan for the reference generator 530, which generates a reference signal N$_{ref}$ for use by the multi-variate process estimator 531.

In the present embodiment, the multi-variate process estimator 531 includes a pseudo-inverse, as is known to those of skill in the art. In another embodiment, the multi-variate process estimator 531 is formed by a joint process estimator and a low pass filter. Details of a suitable joint process estimator are provided in U.S. Pat. No. 5,632,272, incorporated by reference herein. However, it will be understood by those of skill in the art that a variety of such processing structures may be utilized. For example, in another embodiment, a correlation canceller, an adaptive linear combiner, an adaptive noise filter, an adaptive noise canceller, an adaptive linear lattice, a neural network, a radial basis, or a voltera are used individually or in combination, instead of or in addition to the Pseudo-Inverse embodiment of the multi-variate process estimator 531. Such processing structures are well known to those of skill in the art, and require no further explanation herein.

It should be understood that the scan values could be chosen to provide higher or lower resolution than 117 scan values. In one embodiment, the scan values are non-uniformly spaced.

As illustrated in FIG. 10, the reference processor 530 accepts the saturation axis scan values as an input and provides a reference signal N$_{ref}$ as an output. However, in another embodiment, saturation axis scan value are provided to a saturation equation module (not shown). In such embodiment, the saturation equation module provides outputs "$r_n$" that correspond to the plurality of scan value discussed above. The saturation equation simply provides a known ratio that corresponds to the saturation value received as an input based upon data contained within a look-up table, or based upon a known polynomial relationship between the saturation axis scan values and the output "$r_n$".

When a saturation equation module is employed, the ratio "$r_n$" is provided by the saturation equation module as an input to the reference generator 530, along with the sample packets for each of the n light wavelengths. When a saturation equation module is not employed, as illustrated in FIG. 10, a plurality of "$r_n$" values are provided as the saturation axis. In one embodiment, the "$r_n$" values are represented as p(SaO$_{2\_scan}$), a row vector of known constants. The reference generator 530 process the inputs as follows.

The reference generator 530 output N$_{ref}$ is a vector which equals p(SaO$_{2\_scan}$)x, where x is a vector of the normalized plethysmographic waveforms for each of the n wavelengths of light signals $x_i$ (such as outputs 542) and p(SaO$_{2\_scan}$) is a row vector of known constants.

$$\rho(SaO_{2\_scan}) = f^{-1}(SaO_{2\_scan})b^T - \alpha^T, \rho \in R^{1 \times n}.$$

The vector x is provided as the outputs 542 illustrated in FIG. 10. The SaO$_{2\_scan}$ values are the "$r_n$" values provided as the saturation axis, and a and b are known constants defined based on fitting and/or calibration using experimental data and/or models. This operation is completed for each of the saturation scan values (e.g., 117 possible values in the present embodiment). Accordingly, the resultant data can be described as 117 reference signal vectors of 570 data points each, hereinafter referred to as the reference signal vectors. This data can be stored in an array or any such data structure as is well known to those of skill in the art.

In the present embodiment, as described above, the outputs 542 are also provided to a signal selector module 536. One of the output signals 542 is selected by the signal selector module 536 for further processing by the multi-variate process estimator 531. The selected signal is referred to as $X_{sel}$. It is understood by those of skill in the art that any one of the output signals 542 may be selected by the signal selector module 536 for further processing.

In one embodiment, the multi-variate process estimator 531 includes a pseudo-inverse, which is used to determine a weight vector w associated with the reference signal $N_{ref}$ and the selected signal. In one embodiment, the multi-variate process estimator 531 creates multiple single-column vectors of time-shifted data from the reference signal $N_{ref}$. For example, in one embodiment, the multi-variate process estimator 531 creates single-column vectors A, where:

$$A = \begin{bmatrix} \begin{bmatrix} N_{ref\_1} \\ N_{ref\_2} \\ N_{ref\_3} \\ N_{ref\_4} \\ \vdots \end{bmatrix} \begin{bmatrix} N_{ref\_7} \\ N_{ref\_8} \\ N_{ref\_9} \\ N_{ref\_10} \\ \vdots \end{bmatrix} \begin{bmatrix} N_{ref\_13} \\ N_{ref\_14} \\ N_{ref\_15} \\ N_{ref\_16} \\ \vdots \end{bmatrix} \cdots \end{bmatrix}$$

In such embodiment, a pseudo-inverse is determined as $(A^T A)^{-1} A^T$. The weight vector w may then be determined by multiplying the pseudo-inverse by the selected signal ($x_{sel}$) from the signal select module 536. The resulting vector w may be expressed as: $w=(A^T A)^{-1} A^T x_{sel}$. The output vectors w of the multi-variate process estimator 531 are provided to a master power curve module 554 and a divide into equal bins module 556.

The divide into equal bins module 556 divides each of the output vectors into bins having equal numbers of data points. In one embodiment, the divide into equal bins module 556 divides each of the output vectors into five bins, each containing the same number of data points (e.g., with 120 data points per vector, each bin could have 24 data points). Each bin is then provided to a bin power curves module 558.

Figure 11:
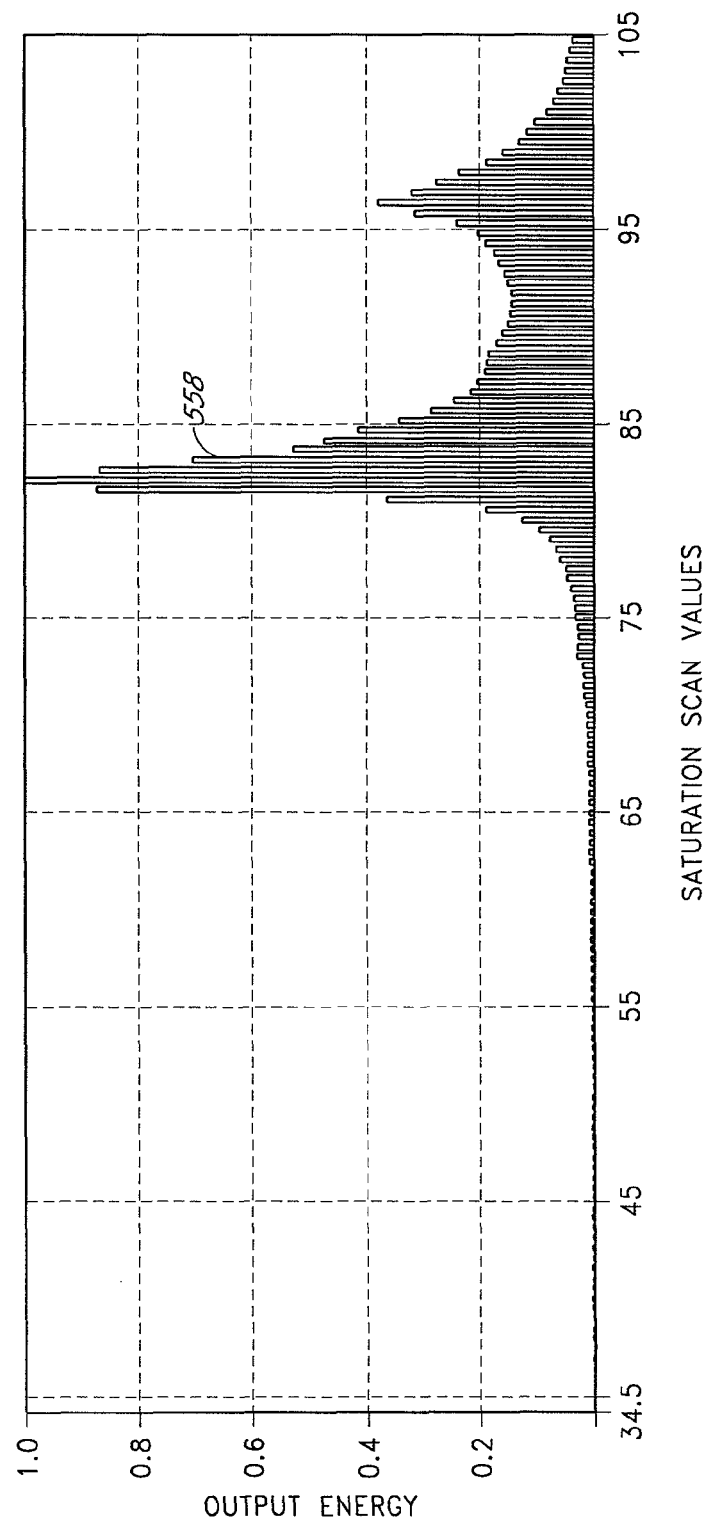
FIG. 11 illustrates a saturation transform curve in accordance with one embodiment of the present invention.

In one embodiment, the master power curve module 554 performs a saturation transform as follows. For each output vector, the sum of the squares of the data points is determined. This provides a sum of squares value corresponding to each output vector (each output vector corresponding to one of the saturation scan values). These values provide the basis for a master power curve 555, as further represented in FIG. 11. The horizontal axis of the power curve represents the saturation axis scan values and the vertical axis represents the sum of squares value (or output energy) for each output vector. In one embodiment, as depicted in FIG. 11, each of the sum of squares is plotted with the magnitude of the sum of squares value plotted on the vertical "energy output" axis at the point on the horizontal axis of the corresponding saturation scan value which generated that output vector. This results in a master power curve 558, an example of which is depicted in FIG. 11. This provides a saturation transform in which the spectral content of the attenuated energy is examined by looking at every possible saturation value and examining the output value for the assumed saturation value. As will be understood, where the inputs to the multi-variate process estimator 531 are mostly correlated, the sum of squares for the corresponding output vector of the multi-variate process estimator 531 will be very low. Conversely, where the correlation between the first and second inputs to the multi-variate process estimator 531 are not significantly correlated, the sum of squares of the output vector will be high. Accordingly, where the spectral content of the reference signal and the first input to the multi-variate process estimator 531 are made up mostly of physiological (e.g., movement of venous blood due to respiration) and nonphysiological (e.g., motion induced) noise, the output energy will be low. Where the spectral content of the reference signal and the first input to the multi-variate process estimator 531 are not correlated, the output energy will be much higher.

A corresponding transform is completed by the Bin Power Curves module 558, except a saturation transform power curve is generated for each bin. The resulting power curves are provided as the outputs of the saturation transform module 406.

In general, in accordance with the signal model embodiment of the present invention, there will be two peaks in the power curves, as depicted in FIG. 11. One peak corresponds to the arterial oxygen saturation of the blood, and one peak corresponds to the venous oxygen concentration of the blood. With reference to the signal model of the present invention, the peak corresponding to the highest saturation value (not necessarily the peak with the greatest magnitude) corresponds to the proportionality coefficient $r_a$. In other words, the proportionality coefficient $r_a$ corresponds to the ratio which will be measured for the arterial saturation. Similarly, peak that corresponds to the lowest saturation value (not necessarily the peak with the lowest magnitude) will generally correspond to the venous oxygen saturation, which corresponds to the proportionality coefficient $r_v$ in the signal model of the present invention. Therefore, the proportionality coefficient $r_v$ will be a ratio corresponding to the venous oxygen saturation.

Figure 12:
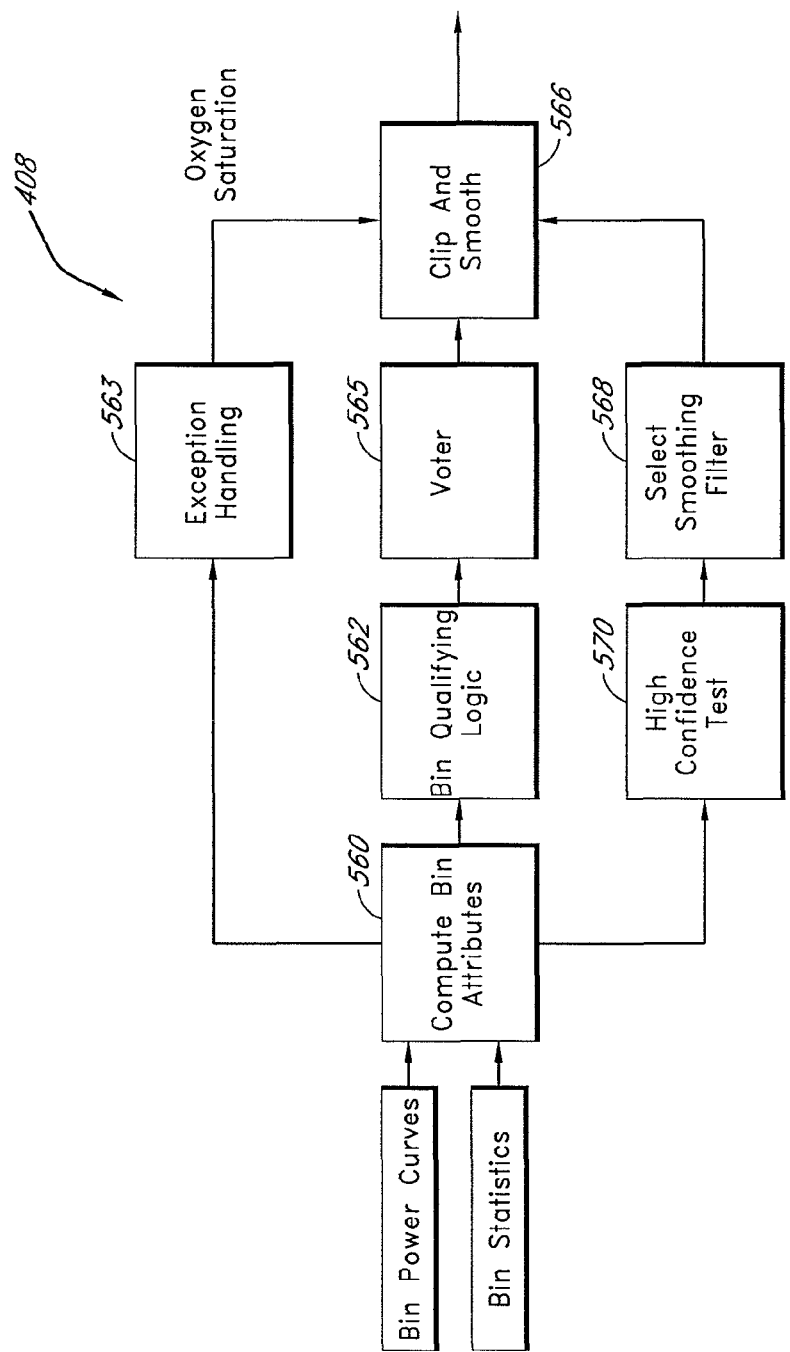
FIG. 12 illustrates a block diagram of the operation of one embodiment of the saturation calculation module of FIG. 6.

In order to obtain arterial oxygen saturation, the peak in the power curves corresponding to the highest saturation value could be selected. However, to improve confidence in the value, further processing is completed. FIG. 12 illustrates the operation of the saturation calculation module 408 based upon the output of the saturation transform module 406 and the output of the statistics module 404. As depicted in FIG. 12, the bin power curves and the bin statistics are provided to the saturation calculation module 408. In the present embodiment, the master power curves are not provided to the saturation module 408 but can be displayed for a visual check on system operation. The bin statistics contain the normalized RMS values for each of the wavelengths signals, the seed saturation value, and a value representing the cross-correlation between the various wavelengths's signals, as described in greater detail above with respect to the statistics module 404 of FIG. 9.

The saturation calculation module 408 first determines a plurality of bin attributes as represented by the compute bin attributes module 560. The compute bin attributes module 560 collects a data bin from the information from the bin power curves and the information from the bin statistics. In the present embodiment, this operation involves placing the saturation value of the peak from each power curve corresponding to the highest saturation value in the data bin. In the present embodiment, the selection of the highest peak is performed by first computing the first derivative of the power curve in question by convolving the power curve with a smoothing differentiator filter function. In the present embodiment, the smoothing differentiator filter function (using a FIR filter) has the following coefficients:

0.014964670230367
0.098294046682706
0.204468276324813
2.717182664241813
5.704485606695227
0.000000000000000
−5.704482606695227
−2.717182664241813
−0.204468276324813
−0.098294046682706
−0.014964670230367

This filter performs the differentiation and smoothing. Next, each point in the original power curve in question is evaluated and determined to be a possible peak if the following conditions are met: (1) the point is at least 2% of the maximum value in the power curve; and (2) the value of the first derivative changes from greater than zero to less than or equal to zero. For each point that is found to be a possible peak, the neighboring points are examined and the largest of the three points is considered to be the true peak.

The peak width for these selected peaks is also calculated. The peak width of a power curve in question is computed by summing all the points in the power curve and subtracting the product of the minimum value in the power curve and the number of points in the power curve. In the present embodiment, the peak width calculation is applied to each of the bin power curves. The maximum value is selected as the peak width.

In addition, the RMS value from the entire snapshot, the individual wavelengths's RMS values, the seed saturation value for each bin, and the cross correlation between the n wavelengths's signals from the statistics module 404 are also placed in the data bin. The attributes are then used to determine whether the data bin consists of acceptable data, as represented in a bin qualifying logic module 562.

If the correlation is too low, the bin is discarded. If the saturation value of the selected peak for a given bin is lower than the seed saturation for the same bin, the peak is replaced with the seed saturation value. If any wavelength's RMS value is below a threshold, the bins are all discarded, and no saturation value is provided, because the measured signals are considered to be too small to obtain meaningful data. If no bins contain acceptable data, the exception handling module 563 provides a message to the display 336 that the data is erroneous.

If some bins qualify, those bins that qualify as having acceptable data are selected, and those that do not qualify are replaced with the average of the bins that are accepted. Each bin is given a time stamp in order to maintain the time sequence. A voter operation 565 examines each of the bins and selects the three highest saturation values. These values are forwarded to a clip and smooth operation 566.

The clip and smooth operation 566 performs averaging with a low pass filter. The low pass filter provides adjustable smoothing as selected by a select smoothing filter module 568. The select smoothing filter module 568 performs its operation based upon a confidence determination performed by a high confidence test module 570. The high confidence test is an examination of the peak width for the bin power curves. The width of the peaks provides some indication of motion by the patient, wherein wider peaks indicate motion. Therefore, if the peaks are wide, the smoothing filter is slowed down. If peaks are narrow, the smoothing filter speed is increased. Accordingly, the smoothing filter 566 is adjusted based on the confidence level. The output of the clip and smooth module 566 provides the oxygen saturation values in accordance with one embodiment of the present invention.

In one embodiment, the clip and smooth filter 566 takes each new saturation value and compares it to the current saturation value. If the magnitude of the difference is less than 16 (percent oxygen saturation) then the value is pass. Otherwise, if the new saturation value is less than the filtered saturation value, the new saturation value is changed to 16 less than the filtered saturation value. If the new saturation value is greater than the filtered saturation value, then the new saturation value is changed to 16 more than the filtered saturation value.

During high confidence (no motion), the smoothing filter is a simple one-pole or exponential smoothing filter which in one embodiment is computed as follows:

$$y(n) = 0.6 * x(n) + 0.4 * y(n-1)$$

where $x(n)$ is the clipped new saturation value, and $y(n)$ is the filtered saturation value.

During motion condition, a three-pole infinite impulse response (IIR) filter is used. Its characteristics are controlled by three time constants $t_a$, $t_b$, and $t_c$ with values of 0.985, 0.900, and 0.94 respectively. The coefficients for a direct form I, IIR filter are computed from these time constants using the following relationships:

$$a_0 = 0$$

$$a_1 = t_b + (t_c)(t_a + t_b)$$

$$a_2 = (-t_b)(t_c)(t_a + t_b + (t_c)(t_a))$$

$$a_3 = (t_b)^2 (t_c)^2 (t_a)$$

$$b_0 = 1 - t_b - (t_c)(t_a + (t_c)(t_b))$$

$$b_1 = 2(t_b)(t_c)(t_a - 1)$$

$$b_2 = (t_b)(t_c)(t_b + (t_c)(t_a) - (t_b)(t_c)(t_a) - t_a)$$

It is well understood by those of skill in the art that the normalized plethysmographic waveforms of the multi-wavelength physiological monitor may be utilized to determine the pulse rate of the patient. For example, in one embodiment, the normalized plethysmographic waveforms of the multi-wavelength physiological monitor, illustrated as lines $\lambda_1$ RMS, $\lambda_2$ RMS, ... $\lambda_n$ RMS in FIG. 9, or the outputs 542 of FIG. 10 may be used to determine the patient's pulse rate. In one embodiment, a Fourier transform is performed on at least one of the normalized plethysmographic waveforms to convert the data of the waveform from the time domain into the frequency domain using methods well known to those of skill in the art. In one embodiment, the first harmonic of the frequency data is identified as the patient's pulse rate.

Other methods of determining pulse rate or heart rate from normalized plethysmographic data is disclosed in U.S. Pat. No. 5,632,272, incorporated by reference in its entirety herein.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

What is claimed is:

1. A physiological monitor for determining blood oxygen saturation of a patient, the physiological monitor comprising:
   a pulse oximetry sensor comprising:
      three or more emitters, wherein each emitter is operative to emit light of a different wavelength; and
      at least one detector adapted to receive light from the three or more emitters after being attenuated by tissue of a medical patient; and
   a processor configured to:
      compute a ratio based at least in part on three or more data signals, each of the three or more data signals indicative of light from one of the three or more emitters after being attenuated by the tissue, wherein the ratio comprises a quotient of a first weighted sum of the data signals multiplied by a first set of vector coefficients and a second weighted sum of the data signals multiplied by a second set of vector coefficients;
      determine blood oxygen saturation based at least in part upon a single blood oxygen saturation curve using said ratio; and
      output the oxygen saturation for display to a clinician.

2. The physiological monitor of claim 1, wherein the first and second sets of vector coefficients are determined based upon calibration data or fitting of experimental data.

3. The physiological monitor of claim 1, wherein the at least one detector provides an output signal based at least in part on the received light and the processor is configured to obtain the three or more data signals from the output signal.

4. The physiological monitor of claim 1, wherein the pulse oximetry sensor is configured to be removably attached to the tissue of the medical patient.

5. The physiological monitor of claim 1, wherein the three or more emitters comprise eight light emitting diodes.

6. The physiological monitor of claim 1, wherein the blood oxygen saturation curve is linear over a range of ratio values, wherein the range of ratio values comprises from about 0.45 to about 1.6.

7. The physiological monitor of claim 1, wherein the blood oxygen saturation curve is linear over a range of blood oxygen saturation values, wherein the range of blood oxygen saturation values comprises from about 75% to about 95%.

8. The physiological monitor of claim 1, wherein the ratio is configured to have reduced tolerance at lower blood oxygen saturation levels compared to a two wavelength blood oxygen saturation system.

9. An apparatus for determining a blood oxygen saturation of a medical patient, the apparatus comprising:
   one or more processors configured to:
      perform a ratio calculation based at least in part on at least three waveforms, each waveform indicative of attenuation of one of at least three wavelengths of light by tissue, wherein the ratio calculation comprises a quotient of a first weighted sum of the at least three waveforms multiplied by a first set of vector coefficients and a second weighted sum of the at least three waveforms multiplied by a second set of vector coefficients, the first and second sets of vector coefficients determined based upon calibration data;
      determine a blood oxygen saturation based at least in part upon a single blood oxygen saturation curve using the ratio; and
      output the oxygen saturation for display to a clinician.

10. The apparatus of claim 9, wherein said blood oxygen saturation curve is linear over a range of blood oxygen saturation values such that the blood oxygen saturation exhibits higher accuracy at lower blood oxygen saturation levels compared to a two wavelength blood oxygen saturation system.

11. The apparatus of claim 10, wherein the range of blood oxygen saturation values comprises about 75% to about 95%.

12. The apparatus of claim 9, wherein the ratio is configured to have reduced tolerance at lower blood oxygen saturation levels compared to a two wavelength blood oxygen saturation system.

13. A method of determining the blood oxygen saturation of a patient, the method comprising:
   under control of a hardware processor,
      receiving at least three data signals, each of the data signals corresponding to one of at least three wavelengths of light that have been attenuated by tissue;
      calculating a ratio with one or more processors based at least in part on the at least three data signals, wherein the ratio comprises a quotient of a first weighted sum of the at least three data signals multiplied by a first set of vector coefficients and a second weighted sum of the at least three data signals multiplied by a second set of vector coefficients;
      determining a blood oxygen saturation based at least in part on a single blood oxygen saturation curve using the ratio; and
      outputting the blood oxygen saturation for display to a clinician.

14. The method of claim 13, wherein said blood oxygen saturation curve is linear over a range of blood oxygen saturation values.

15. The method of claim 14, wherein the range of blood oxygen saturation values comprises about 75% to about 95%.

16. The method of claim 13, wherein the ratio exhibits greater linearity over a first range of ratio values compared to a linearity over a second range of ratio values in a two-wavelength blood oxygen saturation system.

17. The method of claim 13, further comprising generating a composite signal based at least in part on output signals from the at least three wavelengths of light that have been attenuated by tissue and demodulating said composite signal to yield the at least three data signals.

18. The method of claim 13, further comprising determining the at least three data signals by determining an RMS value of each of at least three output signals from the at least three wavelengths of light that have been attenuated by tissue.

* * * * *